US008655037B2

(12) United States Patent  
Christiansen et al.

(10) Patent No.: US 8,655,037 B2
(45) Date of Patent: Feb. 18, 2014

(54) COMPARTMENT SEGREGATION BY PIXEL CHARACTERIZATION USING IMAGE DATA CLUSTERING

(71) Applicant: HistoRx, Inc., New Haven, CT (US)

(72) Inventors: Jason H. Christiansen, Glastonbury, CT (US); Robert Pinard, New Haven, CT (US); Mark Gustavson, Niantic, CT (US); Brian Bourke, Hamden, CT (US); Dylan M. Reilly, Middletown, CT (US); Gregory R. Tedeschi, Cromwell, CT (US)

(73) Assignee: HistoRx, Inc., New Haven, CT (US)

( * ) Notice: Subject to any disclaimer, the term of this patent is extended or adjusted under 35 U.S.C. 154(b) by 0 days.

(21) Appl. No.: 13/715,937

(22) Filed: Dec. 14, 2012

(65) Prior Publication Data

US 2013/0216111 A1    Aug. 22, 2013

Related U.S. Application Data

(62) Division of application No. 12/153,171, filed on May 14, 2008, now Pat. No. 8,335,360.

(60) Provisional application No. 60/917,853, filed on May 14, 2007.

(51) Int. Cl.
    *G06K 9/00*    (2006.01)
(52) U.S. Cl.
    USPC .......................................... 382/128; 382/133
(58) Field of Classification Search
    USPC ........................................................ 382/128
    See application file for complete search history.

(56) References Cited

U.S. PATENT DOCUMENTS

| | | | |
|---|---|---|---|
| 1,914,322 | A | 6/1933 | Bickley |
| 3,958,122 | A | 5/1976 | Jowett et al. |
| 4,480,189 | A | 10/1984 | Miyake et al. |
| 4,557,599 | A | 12/1985 | Zimring |
| 4,859,062 | A | 8/1989 | Thurn et al. |

(Continued)

FOREIGN PATENT DOCUMENTS

| | | |
|---|---|---|
| CA | 2690612 A1 | 11/2008 |
| CA | 2737116 A1 | 3/2010 |

(Continued)

OTHER PUBLICATIONS

Berger et al., "Automated Quantitative Analysis of HDM2 Expression in Malignant Melanoma Shows Association with Early-Stage Disease and Improved Outcome," Cancer Research, vol. 64, Dec. 2004, 8767-8772, pp. 8767-8772.

(Continued)

*Primary Examiner* — Clayton E Laballe  
*Assistant Examiner* — Leon W Rhodes, Jr.  
(74) *Attorney, Agent, or Firm* — Gilberto M. Villacorta; Daniel R. Shelton; Foley & Lardner, LLP

(57) ABSTRACT

The present invention relates generally to improved methods of defining areas or compartments within which biomarker expression is detected and quantified. In particular, the present invention relates to automated methods for delineating marker-defined compartments objectively with minimal operator intervention or decision making. The method provides for precise definition of tissue, cellular or subcellular compartments particularly in histological tissue sections in which to quantitatively analyzing protein expression.

14 Claims, 19 Drawing Sheets

(56) References Cited

U.S. PATENT DOCUMENTS

| | | | |
|---|---|---|---|
| 4,892,817 | A | 1/1990 | Pawlak |
| 4,902,131 | A | 2/1990 | Yamazaki et al. |
| 4,904,088 | A | 2/1990 | Blazek et al. |
| 4,910,398 | A | 3/1990 | Komatsu et al. |
| 4,912,034 | A | 3/1990 | Kalra et al. |
| 4,927,266 | A | 5/1990 | Sugiura et al. |
| 5,015,098 | A | 5/1991 | Berg et al. |
| 5,020,169 | A | 6/1991 | Hamada et al. |
| 5,068,909 | A | 11/1991 | Rutherford et al. |
| 5,070,455 | A | 12/1991 | Singer et al. |
| 5,097,119 | A | 3/1992 | Breitmeier |
| 5,115,673 | A | 5/1992 | Kline et al. |
| 5,126,577 | A | 6/1992 | Trent |
| 5,244,787 | A | 9/1993 | Key et al. |
| 5,254,845 | A | 10/1993 | Burgess et al. |
| 5,309,108 | A | 5/1994 | Maeda et al. |
| 5,422,018 | A | 6/1995 | Saunders et al. |
| 5,427,910 | A | 6/1995 | Kamentsky et al. |
| 5,432,054 | A | 7/1995 | Saunders et al. |
| 5,439,649 | A | 8/1995 | Tseung et al. |
| 5,489,386 | A | 2/1996 | Saunders |
| 5,492,837 | A | 2/1996 | Naser-Kolahzadeh et al. |
| 5,517,193 | A | 5/1996 | Allison et al. |
| 5,523,207 | A | 6/1996 | Kamentsky et al. |
| 5,561,556 | A | 10/1996 | Weissman |
| 5,578,452 | A | 11/1996 | Shi et al. |
| 5,587,833 | A | 12/1996 | Kamentsky |
| 5,602,674 | A | 2/1997 | Weissman et al. |
| 5,633,945 | A | 5/1997 | Kamentsky |
| 5,672,881 | A | 9/1997 | Striepeke et al. |
| 5,682,567 | A | 10/1997 | Spruck et al. |
| 5,694,212 | A | 12/1997 | Weissman |
| 5,717,198 | A | 2/1998 | Broude et al. |
| 5,731,156 | A | 3/1998 | Golbus |
| 5,784,529 | A | 7/1998 | Richmond |
| 5,880,473 | A | 3/1999 | Ginestet |
| 5,885,840 | A | 3/1999 | Kamentsky et al. |
| 5,889,881 | A | 3/1999 | MacAulay et al. |
| 5,916,750 | A | 6/1999 | Iyer et al. |
| 5,948,359 | A | 9/1999 | Kalra et al. |
| 5,962,234 | A | 10/1999 | Golbus |
| 5,978,497 | A | 11/1999 | Lee et al. |
| 6,002,788 | A | 12/1999 | Luther |
| 6,026,174 | A | 2/2000 | Palcic et al. |
| 6,031,930 | A | 2/2000 | Bacus et al. |
| 6,049,220 | A | 4/2000 | Borden et al. |
| 6,052,190 | A | 4/2000 | Sekowski et al. |
| 6,087,134 | A | 7/2000 | Saunders |
| 6,101,265 | A | 8/2000 | Bacus et al. |
| 6,130,323 | A | 10/2000 | Su et al. |
| 6,134,354 | A | 10/2000 | Lee et al. |
| 6,137,899 | A | 10/2000 | Lee et al. |
| 6,151,405 | A | 11/2000 | Douglass et al. |
| 6,165,739 | A | 12/2000 | Clatch |
| 6,169,816 | B1 | 1/2001 | Ravkin |
| 6,215,892 | B1 | 4/2001 | Douglass et al. |
| 6,221,607 | B1 | 4/2001 | Tsipouras et al. |
| 6,225,636 | B1 | 5/2001 | Ginestet |
| 6,226,392 | B1 | 5/2001 | Bacus et al. |
| 6,239,868 | B1 | 5/2001 | Jung et al. |
| 6,252,242 | B1 | 6/2001 | Brunfeld et al. |
| 6,259,807 | B1 | 7/2001 | Ravkin |
| 6,270,971 | B1 | 8/2001 | Ferguson-Smith et al. |
| 6,272,235 | B1 | 8/2001 | Bacus et al. |
| 6,292,582 | B1 | 9/2001 | Lin et al. |
| 6,309,601 | B1 | 10/2001 | Juncosa et al. |
| 6,330,349 | B1 | 12/2001 | Hays et al. |
| 6,396,941 | B1 | 5/2002 | Bacus et al. |
| 6,404,906 | B2 | 6/2002 | Bacus et al. |
| 6,404,916 | B1 | 6/2002 | De La Torre-Bueno |
| 6,408,048 | B2 | 6/2002 | Opsal et al. |
| 6,418,236 | B1 | 7/2002 | Ellis et al. |
| 6,445,817 | B1 | 9/2002 | De La Torre-Bueno |
| 6,451,551 | B1 | 9/2002 | Zhan et al. |
| 6,458,585 | B1 | 10/2002 | Vachula et al. |
| 6,466,690 | B2 | 10/2002 | Bacus et al. |
| 6,493,460 | B1 | 12/2002 | MacAulay et al. |
| 6,495,106 | B1 | 12/2002 | Kalra et al. |
| 6,518,554 | B1 | 2/2003 | Zhang |
| 6,522,744 | B1 | 2/2003 | Chiang |
| 6,524,798 | B1 | 2/2003 | Goldbard et al. |
| 6,546,123 | B1 | 4/2003 | McLaren et al. |
| 6,553,135 | B1 | 4/2003 | Douglass et al. |
| 6,589,792 | B1 | 7/2003 | Malachowski |
| 6,631,203 | B2 | 10/2003 | Ellis et al. |
| 6,632,598 | B1 | 10/2003 | Zhang et al. |
| 6,633,662 | B2 | 10/2003 | Ravkin |
| 6,648,506 | B2 | 11/2003 | McGrath et al. |
| 6,671,393 | B2 | 12/2003 | Hays et al. |
| 6,674,058 | B1 | 1/2004 | Miller |
| 6,674,896 | B1 | 1/2004 | Torre-Bueno |
| 6,697,509 | B2 | 2/2004 | De La Torre-Bueno |
| 6,718,053 | B1 | 4/2004 | Ellis et al. |
| 6,746,873 | B1 | 6/2004 | Buchanan et al. |
| 6,777,194 | B1 | 8/2004 | Gerdes et al. |
| 6,778,714 | B1 | 8/2004 | Kipman et al. |
| 6,780,377 | B2 | 8/2004 | Hall et al. |
| 6,800,249 | B2 | 10/2004 | De La Torre-Bueno |
| 6,816,625 | B2 | 11/2004 | Lewis et al. |
| 6,852,986 | B1 | 2/2005 | Lee et al. |
| 6,876,760 | B1 | 4/2005 | Vaisberg et al. |
| 6,881,580 | B2 | 4/2005 | Hall et al. |
| 6,882,873 | B2 | 4/2005 | Samuels et al. |
| 6,900,426 | B2 | 5/2005 | Zhang |
| 6,920,239 | B2 | 7/2005 | Douglass et al. |
| 6,947,583 | B2 | 9/2005 | Ellis et al. |
| 7,006,680 | B2 | 2/2006 | Gulati |
| 7,024,316 | B1 | 4/2006 | Ellison et al. |
| 7,064,829 | B2 | 6/2006 | Li et al. |
| 7,070,951 | B2 | 7/2006 | Zhang et al. |
| 7,084,386 | B2 | 8/2006 | Bernardini et al. |
| 7,113,205 | B2 | 9/2006 | Cappellaro |
| 7,116,354 | B2 | 10/2006 | Rice et al. |
| 7,123,756 | B2 | 10/2006 | Hakamata et al. |
| 7,129,053 | B1 | 10/2006 | Reiter et al. |
| 7,133,543 | B2 | 11/2006 | Verwoerd et al. |
| 7,133,545 | B2 | 11/2006 | Douglass et al. |
| 7,146,062 | B2 | 12/2006 | De La Torre-Bueno et al. |
| 7,171,054 | B2 | 1/2007 | Fiete et al. |
| 7,173,663 | B2 | 2/2007 | Skow et al. |
| 7,177,454 | B2 | 2/2007 | McLaren et al. |
| 7,189,576 | B2 | 3/2007 | Fukuoka et al. |
| 7,190,818 | B2 | 3/2007 | Ellis et al. |
| 7,199,360 | B1 | 4/2007 | Montagu |
| 7,205,154 | B2 | 4/2007 | Corson |
| 7,212,660 | B2 | 5/2007 | Wetzel et al. |
| 7,219,016 | B2 | 5/2007 | Rimm et al. |
| 7,224,470 | B2 | 5/2007 | Vaux et al. |
| 7,224,839 | B2 | 5/2007 | Zeineh |
| 7,229,774 | B2 | 6/2007 | Chinnaiyan et al. |
| 7,233,340 | B2 | 6/2007 | Hughes et al. |
| 7,236,623 | B2 | 6/2007 | Chapoulaud et al. |
| 7,257,267 | B2 | 8/2007 | Recht |
| 7,269,280 | B2 | 9/2007 | Hiroi et al. |
| 7,272,252 | B2 | 9/2007 | De La Torre-Bueno et al. |
| 7,292,275 | B2 | 11/2007 | Masuyama |
| 7,316,907 | B2 | 1/2008 | Yu et al. |
| 7,330,250 | B2 | 2/2008 | Gip et al. |
| 7,332,290 | B2 | 2/2008 | Rubin et al. |
| 7,369,696 | B2 | 5/2008 | Arini et al. |
| 7,376,256 | B2 | 5/2008 | Kirsch et al. |
| 7,383,134 | B2 | 6/2008 | Piper et al. |
| 7,440,637 | B2 | 10/2008 | Schechner et al. |
| 7,474,777 | B2 | 1/2009 | Kirsch et al. |
| 7,474,847 | B2 | 1/2009 | Nikkanen et al. |
| 7,557,963 | B2 | 7/2009 | Bhattacharjya |
| 7,639,350 | B2 | 12/2009 | Noguchi et al. |
| 7,666,663 | B2 | 2/2010 | Sugiyama et al. |
| 7,709,222 | B2 | 5/2010 | Rimm et al. |
| 7,760,927 | B2 | 7/2010 | Gholap et al. |
| 7,767,393 | B2 | 8/2010 | Chinnaiyan et al. |
| 7,826,648 | B2 | 11/2010 | Arai |
| 7,847,239 | B2 | 12/2010 | Lu et al. |
| 7,873,215 | B2 | 1/2011 | Xiao et al. |

(56) References Cited

U.S. PATENT DOCUMENTS

| | | | |
|---|---|---|---|
| 7,899,623 B2 | 3/2011 | Marcelpoil et al. | |
| 7,907,271 B2 | 3/2011 | Christiansen et al. | |
| 7,941,275 B2 | 5/2011 | Gholap et al. | |
| 8,160,348 B2 | 4/2012 | Pinard et al. | |
| 2002/0141049 A1 | 10/2002 | Masuyama | |
| 2002/0177149 A1* | 11/2002 | Rimm et al. | 435/6 |
| 2003/0138827 A1 | 7/2003 | Kononen et al. | |
| 2003/0215936 A1 | 11/2003 | Kallioniemi et al. | |
| 2004/0014165 A1 | 1/2004 | Keidar et al. | |
| 2004/0027618 A1 | 2/2004 | Nakamura et al. | |
| 2004/0056966 A1 | 3/2004 | Schechner et al. | |
| 2004/0085475 A1 | 5/2004 | Skow et al. | |
| 2004/0215087 A1 | 10/2004 | Genero et al. | |
| 2005/0037406 A1 | 2/2005 | De La Torre-Bueno et al. | |
| 2005/0105787 A1 | 5/2005 | Gulati | |
| 2005/0136509 A1 | 6/2005 | Gholap et al. | |
| 2005/0142579 A1 | 6/2005 | Sugiyama et al. | |
| 2005/0196040 A1 | 9/2005 | Ohara | |
| 2005/0266395 A1 | 12/2005 | Gholap et al. | |
| 2005/0282179 A1 | 12/2005 | Martin et al. | |
| 2006/0001765 A1 | 1/2006 | Suda | |
| 2006/0014238 A1 | 1/2006 | Gholap et al. | |
| 2006/0015262 A1 | 1/2006 | Gholap et al. | |
| 2006/0063190 A1 | 3/2006 | Fischer et al. | |
| 2006/0078926 A1 | 4/2006 | Marcelpoil et al. | |
| 2006/0127946 A1 | 6/2006 | Montagu et al. | |
| 2006/0160169 A1 | 7/2006 | Marcotte et al. | |
| 2006/0166253 A1 | 7/2006 | Kononen et al. | |
| 2006/0188140 A1 | 8/2006 | Gholap et al. | |
| 2006/0211017 A1 | 9/2006 | Chinnaiyan et al. | |
| 2006/0239533 A1 | 10/2006 | Tafas et al. | |
| 2006/0275844 A1 | 12/2006 | Linke et al. | |
| 2007/0114388 A1 | 5/2007 | Ogawa et al. | |
| 2007/0154958 A1 | 7/2007 | Hamann et al. | |
| 2007/0207489 A1 | 9/2007 | Pestano et al. | |
| 2008/0013816 A1 | 1/2008 | Rimm et al. | |
| 2008/0026415 A1 | 1/2008 | Rimm et al. | |
| 2008/0118437 A1 | 5/2008 | Pienta et al. | |
| 2008/0153098 A1 | 6/2008 | Rimm et al. | |
| 2008/0153877 A1 | 6/2008 | Adimoolam et al. | |
| 2008/0309929 A1 | 12/2008 | Christiansen et al. | |
| 2009/0034823 A1 | 2/2009 | Christiansen et al. | |
| 2009/0074266 A1 | 3/2009 | Pinard et al. | |
| 2009/0074282 A1 | 3/2009 | Pinard et al. | |
| 2009/0086046 A1 | 4/2009 | Reilly et al. | |
| 2009/0167850 A1 | 7/2009 | Bruno et al. | |
| 2010/0136549 A1 | 6/2010 | Christiansen et al. | |
| 2011/0116086 A1 | 5/2011 | Christiansen et al. | |
| 2011/0116087 A1 | 5/2011 | Christiansen et al. | |
| 2011/0228993 A1 | 9/2011 | Reilly et al. | |

FOREIGN PATENT DOCUMENTS

| | | |
|---|---|---|
| EP | 0 709 667 A2 | 5/1996 |
| EP | 0 549 905 B1 | 4/1999 |
| EP | 0 977 981 A1 | 2/2000 |
| EP | 0 720 114 B1 | 1/2001 |
| EP | 1 065 496 A2 | 3/2001 |
| EP | 1 202 563 A1 | 5/2002 |
| EP | 1 251 179 A2 | 10/2002 |
| EP | 1 300 713 A2 | 4/2003 |
| EP | 1 3329 513 A1 | 7/2003 |
| EP | 1 347 285 A1 | 9/2003 |
| EP | 1 779 088 | 2/2006 |
| EP | 1 502 098 B1 | 9/2008 |
| GB | 2 305 723 A | 4/1997 |
| GB | 2 395 263 A | 5/2004 |
| GB | 2 396 406 A | 6/2004 |
| GB | 2 406 908 A | 4/2005 |
| GB | 2 423 150 A | 8/2006 |
| GB | 2 430 026 A | 3/2007 |
| JP | 02-232550 A | 9/1990 |
| JP | 04-315119 A | 11/1992 |
| JP | 05-249102 A | 9/1993 |
| JP | 07-030753 | 1/1995 |
| JP | 11-183381 A | 7/1999 |
| JP | 2001-211896 A | 8/2001 |
| JP | 2003-284713 A | 10/2003 |
| JP | 2003-294734 A | 10/2003 |
| JP | 2004-354346 A | 12/2004 |
| JP | 2005-070537 A | 3/2005 |
| JP | 2005-535892 A | 11/2005 |
| JP | 2005-331394 A | 12/2005 |
| JP | 2006-194711 A | 7/2006 |
| JP | 2007-127485 A | 5/2007 |
| JP | 2007-232631 A | 9/2007 |
| JP | 2007-271484 A | 10/2007 |
| JP | 2007-278984 A | 10/2007 |
| WO | WO-95/34050 A1 | 12/1995 |
| WO | WO-96/09604 A1 | 3/1996 |
| WO | WO-96/09605 A1 | 3/1996 |
| WO | WO-96/23898 A1 | 8/1996 |
| WO | WO-98/07022 A1 | 2/1998 |
| WO | WO-99/30278 A1 | 6/1999 |
| WO | WO-00/64147 A1 | 10/2000 |
| WO | WO-00/79326 A1 | 12/2000 |
| WO | WO-02/056584 A1 | 7/2002 |
| WO | WO-02-067188 A2 | 8/2002 |
| WO | WO-02/086498 A1 | 10/2002 |
| WO | WO-02/099429 A1 | 12/2002 |
| WO | WO-03/008963 A1 | 1/2003 |
| WO | WO-03/056343 A2 | 7/2003 |
| WO | WO-03/093810 A1 | 11/2003 |
| WO | WO-03/097850 | 11/2003 |
| WO | WO-03/098522 A1 | 11/2003 |
| WO | WO-2004/017052 A2 | 2/2004 |
| WO | WO-2004/025569 A2 | 3/2004 |
| WO | WO-2004/059288 A2 | 7/2004 |
| WO | WO-2005/027015 A2 | 3/2005 |
| WO | WO-2005/033706 A1 | 4/2005 |
| WO | WO-2005/045734 A1 | 5/2005 |
| WO | WO-2005/076197 A2 | 8/2005 |
| WO | WO-2005/076216 A2 | 8/2005 |
| WO | WO-2005/077263 A2 | 8/2005 |
| WO | WO-2005/096225 A1 | 10/2005 |
| WO | WO-2005/114578 A1 | 12/2005 |
| WO | WO-2006/036726 A1 | 4/2006 |
| WO | WO-2006/036788 A2 | 4/2006 |
| WO | WO-2006/039396 A2 | 4/2006 |
| WO | WO-2006/054991 A1 | 5/2006 |
| WO | WO 2006/083969 A2 | 8/2006 |
| WO | WO-2006/102233 A2 | 9/2006 |
| WO | WO-2006/105519 A2 | 10/2006 |
| WO | WO 2006/122251 A2 | 11/2006 |
| WO | WO-2006/133325 A2 | 12/2006 |
| WO | WO-2007/024264 A2 | 3/2007 |
| WO | WO-2007/133465 A2 | 11/2007 |
| WO | WO-2008/012771 A2 | 1/2008 |
| WO | WO-2008/143849 A2 | 11/2008 |
| WO | WO-2008/156669 A1 | 12/2008 |
| WO | WO-2009/020621 A1 | 2/2009 |
| WO | WO-2009/020972 A2 | 2/2009 |
| WO | WO-2009/029810 A1 | 3/2009 |
| WO | WO-2010/033508 A1 | 3/2010 |

OTHER PUBLICATIONS

Butler "Enzyme-Linked Immunosorbent Assay," Journal of Immunoassay, vol. 21(2&3), 2000, pp. 165-209.

Camp et al., "Quantitative Analysis of Breast Cancer Tissue Microarrays Shows That Both High and Normal Levels of HER2 Expression are Associated with Poor Outcome," Cancer Research, vol. 63, Apr. 2003, pp. 1445-1448.

Camp et al., "X-Title: A New Bio-Informatics Tool for Biomarker Assessment and Outcome-Based Cut-Point Optimization," Clinical Cancer Research, vol. 10, 2004, pp. 7252-7259.

Camp et al., "Automated Subcellular Localization and Quantification of Protein Expression in Tissue Microarrays," New Technology—Nature Medicine, 2002, vol. 8, No. 11, pp. 1323-1327.

Chen et al., "Ratio-Based Decisions and the Quantitative Analysis of cDNA Microarray Images," Journal of Biomedical Optics, SPIE, Bellingham, WA, vol. 2, No. 4, Oct. 1, 1997, pp. 364-374.

(56) References Cited

OTHER PUBLICATIONS

Chung et al., "Tissue Microarray Analysis of B-Certain in Colorectal Cancer Shows Nuclear Phospho-B-catenin is Associated with a Better Prognosis," Clinical Cancer Research, vol. 7, pp. 4013-2010, Dec. 2001.

Communication mailed Apr. 28, 2010 in European Appln No. 08754418.5.

Cregger et al., "Immunohistochemistry and Quantative Analysis of Protein Expression," Arch Pathol Lab Med, vol. 130, Jul. 2006, pp. 1026-1030.

Dell'anna et al., "An Automated Procedure to Properly Handle Digital Images in Large Scale Tissue Microarray Experiments", Computer Methods and Programs in Biomedicine, Elsevier, Amsterdam, NL, vol. 79, No. 3, Sep. 1, 2005, pp. 197-208.

Demir et al, "Automated cancer diagnosis based on histopathological images: a systematic survey," Rensselaer Polytechnic Institute, Department of Computer Science, Technical Report TR-05-09, Published 2005.

Dolled-Filhart et al., "Classification of Breast Cancer Using Genetic Algorithms and Tissue Microarrays," Clin Cancer Research, vol. 12(21), pp. 6459-6468, Nov. 1, 2006, www.aacrjournals.org.

Dolled-Filhart et al., "Quantitive In Situ Analysis of B-Catenin Expression in Breast Cancer Shows Decreased Expression is Associated with Poor Outcome," Cancer Res., vol. 66, No. 10, 2006, pp. 5487-5494.

Dolled-Filhart et al., "Tissue Microarray Analysis of Signal Transducers and Activators of Transcription 3 (Stat3) and Phospho-Stat3 (Tyr705) in Node-Negative Breast Cancer Shows Nuclear Localization Is Associated with a Better Prognosis," Clinical Cancer Research, vol. 9, Feb. 2003, pp. 594-600.

Duggan et al., "Expression Profiling Using cDNA Microarrays," Nature Genetics, Nature Publishing Group, New York, vol. 21, No. Suppl., Jan. 1, 1999, pp. 10-14.

Elias, "Immunoshistopathology a Practical Approach to Diagnosis," American Society of Clinical Pathologists, ASCP Press, Chicago, 1990.

Feng, et al., "Adaptive Kurtosis Optimization Autofocus Algorithm," Journal of Electronics, vol. 23, No. 4, Jul. 2006, pp. 532-534.

Giltnane et al., Technology Insight: "Identification of Biomarkers With Tissue Microarray Technology," Nature Clinical Practice Oncology, vol. 1, No. 2. (Dec. 2004), pp. 104-111.

Gustavson, et al., Mark D., "Development of an Unsupervised Pixel-Based Clustering Algorithm for Compartmentalization of Immunohistochemical Expression Using Automated Quantitative Analysis", Applied Immunohistochemistry, vol. 17, No. 4, Jul. 1, 2009, pp. 329-337.

Handbook of Fluorescent Probes and Research Products, 8th Edition, 2001.

Harvey et al., "Estrogen Receptor Status by Immunohistochemistry is Superior to the Ligand-Binding Assay for Predicting Response to Adjuvant Endocrine Therapy in Breast Cancer," Journal of Clinical Oncology, vol. 17, No. 5, 1999, pp. 1474-1481.

International Search Report and Written Opinion, PCT/US2009/056996, Jan. 25, 2010, 11 pgs.

Jain A.K., et al, "Data Clustering: A Review", ACM Computing Surveys, vol. 31, No. 3, Sep. 1999, pp. 264-323.

Jain, "Fundamentals of Digital Image Processing", Image Analysis and Computer Vision, Chapter 9, Jan. 1, 1989, p. 418.

Jowett, "Tissue In Situ Hybridization: Methods in Animal Development," John Whey & Sons, Inc. And Spektrum Akademischer Verlag, 1997.

Kallioniemi et al., "Tissue Microarray Technology for High-Throughput Molecular Profiling of Cancer," Human Molecular Genetics, vol. 10, No. 7, 2001, pp. 657-662.

Katoh, et al., "Immunoperoxidase Staining for Estrogen and Progesterone Receptors in Archival Formalin Fixed, Paraffin Embedded Breast Carcinomas after Microwave Antigen Retrieval," Biotechnic & Histochemistry, vol. 72, No. 6, pp. 291-298, Nov. 1997.

Kononen et al., "Tissue Microarrays for High-Throughput Molecular Profiling of Tumor Specimens," Nature Medicine, vol. 4, No. 7, Jul. 1998, pp. 844-847.

Leitch, "In Situ Hybridization: A Practical Guide," Oxford BIOS Scientific Publishers, Microscopy Handbooks (1994).

Lillie, "H.J. Conn's Biological Stains: A Handbook on the Nature and Uses of the Dyes Employed in the Biological Laboratory," The Williams & Wilkins Company, copyright 1969, Eighth Edition.

McCabe et al., "Automated Quantitative Analysis (AQUA) of In Situ Protein Expression, Antibody Concentration, and Prognosis," Journal of the National Cancer Institute, vol. 97, No. 24, pp. 1808-1815, Dec. 21, 2005.

McGinty et al., "Double Immunostaining Reveals Distinctions Among Opioid Peptidergic Neurons in the Medical Basal Hypothalamus," Brain Research, vol. 278, pp. 145-153, 1983, Elsevier.

Miller et al., "Emergent Unsupervised Clustering Paradigms with Potential Application to Bioinformatics," Frontiers in Bioscience, vol. 13, Jan. 2008, pp. 677-690.

Molecular Devices, Corp., "GenePix Pro 6.0 Microarray Acquisition and Analysis Software for GenePix Microarray Scanners—User's Guide and Tutorial," Genepix Pro 6.0—Molecular Devices, Corp., Feb. 2005.

Office Action—Communication pursuant to Article 94(3) EPC—for EP 08768439.5—dated Oct. 12, 2012.

Office Action in CN Appln No. 200980137750.0 dated Oct. 25, 2012.

Office Action in JP Appln No. 2010-508400 dated Jul. 31, 2012.

Office Action mailed Aug. 7, 2012 in Japan Application No. 2010-508400, with translation, 7 pgs.

Paik et al., "Benefit from Adjuvant Trastuzumab May Not Be Confined to Patients With IHC 3 and/or FISH Positive Tumors: Central Testing Results from NSABP B-31," vol. 25, 2007, pp. 511.

Perez et al., "HER2 Testing by Local, Central, and Reference Laboratories in Specimens from the North Central Cancer Treatment Group N9831 Intergroup Adjuvant Trial", Journal of Clinical Oncology, vol. 24, 2006, pp. 3032-3038.

Raeside, et al., "Monte Carlo Principles and Application," Phs Med Biol., vol. 21, No. 2, 1976, pp. 181-197.

Rimm et al., "Tissue Microarray: A New Technology for Amplification of Tissue Resources," The Cancer Journal, vol. 7, No. 1, Jan./Feb. 2001, pp. 24-31.

Roth, et al., "Enzyme-based Antigen Localization and Quantitation in Cell and Tissue Samples (Midwestern Assay)," The Journal of Histochemistry & Cytochemistry, vol. 45(12), pp. 1629-1641, 1997.

Rubin et al. "Quantitative determination of expression of the prostate cancer protein alpha-methylacyl-CoA racemase using automated quantitative analysis (AQUA): A novel paradigm for automated and continuous biomarker measurements," American Journal of Pathology, vol. 164, No. 3, Mar. 2004, pp. 831-840.

Sambrook et al., "Molecular Cloning, a Laboratory Manual," 1989, Cold Spring Harbor Laboratory Press, Cold Spring Harbor, N.Y., 30 pages.

Schweitzer et al. "Multiplexed protein profiling on microarrays by rolling-circle amplification," Nature Biotechnology, vol. 20, 2002, pp. 359-365.

Search Report mailed Feb. 17, 2009 in International Appln No. PCT/US2008/006116.

Search Report mailed Jun. 12, 2009 in International Appln No. PCT/US2008/072235.

Search Report mailed Nov. 13, 2008 in International Appln No. PCT/US2008/074817.

Search Report mailed Nov. 18, 2008 in International Appln. No. PCT/US2008/09454.

Search Report mailed Nov. 24, 2008 in International Appln. No. PCT/US2008/007399.

(56) References Cited

OTHER PUBLICATIONS

Snead, et al., "Methodology of Immunohistological Detection of Oestrogen Receptor in Human Breast Carcinoma in Formalin-Fixed, Paraffin-Embedded Tissue: A Comparison with Frozen Section Methodology," Histopathology, vol. 23, pp. 233-238, 1993.

Teverovskiy, et al.,"Automated Localization and Quantificiation of Protein Multiplexes Via Multispectral Fluorescence Imaging", Biomedical Imaging: From Nano to Macro, 2008, ISBI 2008, 5th IEEE International Symposium on, IEEE, Piscataway, NJ, May 14, 2008, pp. 300-303.

Wiemann, et al., Coley's Toxins, Tumor Necrosis Factor and Cancer Research: A Historical Perspective; Pharmacol. Ther., 64:529-564 (1994), Abstract only.

Wolff, et al., Arch Pathol Lab Med., "American Society of Clinical Oncology/College of American Pathologists Guideline Recommendations for Human Epidermal Growth Factor Receptor 2 Testing in Breast Cancer," vol. 131, Jan. 2007, p. 18-43.

Final Office Action mailed Mar. 5, 2013 in U.S. Appl. No. 12/560,129, 18 pages.

* cited by examiner

A

Nuclear

B

Cytoplasmic

Statistics

| | | Cyto_Avg_Trad | Cyto_Avg_AQUAte | Cyto_Avg_Trad_LOG | Cyto_Avg_AQUAte_LOG |
|---|---|---|---|---|---|
| N | Valid | 98 | 98 | 98 | 98 |
| | Missing | 59 | 59 | 59 | 59 |
| Mean | | 1134.67154 | 997.880689 | 9.6461 | 9.4500 |
| Median | | 685.16835 | 641.032300 | 9.4203 | 9.3241 |
| Std. Deviation | | 1131.341508 | 1037.3721254 | 1.15022 | 1.14747 |
| Variance | | 1279933.607 | 1076140.927 | 1.323 | 1.317 |
| Skewness | | 2.292 | 2.504 | .560 | .651 |
| Std. Error of Skewness | | .244 | .244 | .244 | .244 |
| Range | | 5883.409 | 5689.1072 | 4.86 | 5.09 |
| Minimum | | 209.955 | 172.1173 | 7.71 | 7.43 |
| Maximum | | 6093.364 | 5861.2245 | 12.57 | 12.52 |

A
Nuclear

B
Cytoplasmic

| STATISTICS | | Nuc_Avg_Trad | Nuc_Avg_AQUAte | Nuc_Avg_Trad_LOG | Nuc_Avg_AQUAte_LOG |
|---|---|---|---|---|---|
| N | VALID | 154 | 154 | 154 | 154 |
|  | MISSING | 54 | 54 | 54 | 54 |
| MEAN |  | 334.9513 | 327.2717 | 8.1237 | 8.0845 |
| MEDIAN |  | 248.0382 | 250.3658 | 7.9542 | 7.9678 |
| STD. DEVIATION |  | 307.55615 | 274.63550 | .78534 | .80915 |
| VARIANCE |  | 94590.782 | 75424.658 | .617 | .655 |
| SKEWNESS |  | 6.154 | 4.288 | .918 | .825 |
| STD. ERROR OF SKEWNESS |  | .195 | .195 | .195 | .195 |
| RANGE |  | 3204.59 | 2453.33 | 6.25 | 5.83 |
| MINIMUM |  | 42.56 | 43.90 | 5.41 | 5.46 |
| MAXIMUM |  | 3247.15 | 2497.23 | 11.66 | 11.29 |

COMPARTMENT SEGREGATION BY PIXEL CHARACTERIZATION USING IMAGE DATA CLUSTERING

RELATED APPLICATION

This application is a divisional application of application Ser. No. 12/153,171, filed May 14, 2008, now U.S. Pat. No. 8,335,360, which claims the benefit of U.S. Provisional Application Ser. No. 60/917,853, filed May 14, 2007, the entire contents of which are herein incorporated by reference.

BACKGROUND OF THE INVENTION

Automated quantitative analysis of biomarker expression in tissue sections or tissue microarrays presents several challenges, including heterogeneity of tissue sections, sub-cellular localization of staining and the presence of background signal. For example, depending on the type of tumor or tissue section being analyzed, the area of interest may represent nearly the entire sample or only a small percentage. For instance, a pancreatic carcinoma or lobular carcinoma of the breast with substantial desmoplastic response may show stromal tissue representing a large percentage of the total area. If the goal of the assay is to determine epithelial cell expression of a given marker, a protocol must be used that evaluates only that region. The protocol must not only be able to select the region of interest but also normalize it, so that the expression level read from any given area can be compared with that of other areas. Sub-cellular localization presents similar challenges. Automated systems and methods for rapidly analyzing tissue sections, including tissue microarrays, which permit the identification and localization of identified biomarkers within sub-cellular compartments in tissues and other cell containing samples, are needed.

Certain methods (including confocal and convolution/deconvolution microscopy) have been used to quantify expression of proteins at the cellular (or sub-cellular) level within a single high power field. These methods, however, are computationally intensive and laborious techniques that operate on multiple serial images. As a result, the current standard for analysis of immunohistology, is conventional pathologist-based analysis and grading of the sample according to scale.

Automated systems for histological analysis of tissue sections often include methods that either have 1) an operator examining an image of a field of view of a stained tissue and adjusting parameters for optimal analysis conditions or 2) consistent settings that treat an entire data set in the same manner, but an operator is still required to make judgment calls in setting the initial parameters i.e. thresholds. Both of these methods suffer at least the disadvantage that the data is not being treated by a single uniform method that is completely objective. These decisions can influence the output of the system and affect data quality. They also add an extra layer of system complexity in that analysis methods can be adjusted to individual experiments or individual specimens and no universal method is used.

SUMMARY OF THE INVENTION

The present invention relates generally to methods of detecting and quantifying protein expression and identifying marker-defined biological compartments. It is an object of the present invention to provide methods of defining compartments within which biomarker expression is localized and quantified in tissues and cell containing samples, which requires minimal user intervention and provides optimal compartment, including sub-cellular compartment resolution.

In one embodiment, the present invention is directed to a method for defining a first marker defined biological compartment relative to a second marker defined biological compartment present in a biological sample of interest, comprising comparing the intensity in each of the pixel locations in a first high resolution image of the first marker defined biological compartment with the intensity in each of the corresponding pixel locations of a second high resolution image of the second marker defined biological compartment, wherein the first high resolution image was prepared using a first imaging agent that is specific for the first marker defined biological compartment, and wherein the second high resolution image was prepared using a second imaging agent that is specific for the second marker defined biological compartment, wherein differences in pixel intensity define the first marker defined biological compartment relative to the second marker defined biological compartment. In a particular embodiment, the method is automated, e.g., wherein the method is implemented by a computer. In a particular embodiment, the pixels of the two high resolution images are plotted, wherein the axes of the plot comprise the intensity of the first imaging agent and the intensity of the second imaging agent. In particular embodiments, the methods of the present invention optionally comprise i) assigning pixels to a cluster characterized by high first imaging agent intensity and low second imaging agent intensity to the first compartment; ii) assigning pixels to a cluster characterized by high second imaging agent intensity and low first imaging agent intensity to the second compartment; and iii) assigning pixels to a cluster characterized by low first imaging agent intensity and low second imaging agent intensity to background and removing such pixels from further analysis. In a particular embodiment, any of the assigning steps are performed using a clustering algorithm, e.g., a k-means clustering method to determine a cluster membership for each pixel. In a particular embodiment, the methods of the invention optionally comprise assigning remaining pixels with first imaging agent intensity and second imaging agent intensity to either the first compartment or the second compartment based on probability. In a particular embodiment, the methods of the invention optionally comprise assigning those remaining pixels with first imaging agent intensity and second imaging agent intensity to neither the first compartment nor the second compartment. In a particular embodiment, the biological compartment is selected from the group consisting of: a cell type, sub-cellular compartment, a tissue compartment, and a localized cellular or tissue compartment. In a particular embodiment, the biological compartment is a sub-cellular compartment selected from the group consisting of: cell nucleus, cytoplasm, nuclear membrane, cellular membrane, mitochondria, endoplasmic reticulum, peroxisome and lysosome. In a particular embodiment, the biological compartment is a tissue compartment selected from the group consisting of: epithelium, stroma, mesothelia. In a particular embodiment, the sample is a tissue sample, cell preparation or sub cellular fraction. In a particular embodiment, the methods of the invention optionally comprise defining a mask defined by the pixel intensity of the first and/or second imaging agent and defining compartment assignment for only those pixels within the mask. In a particular embodiment, the methods of the invention optionally comprise incubating the sample with a first imaging agent that specifically labels the first marker defined biological compartment, a second imaging agent that specifically labels a second marker defined biological compartment In one embodiment, the present invention is directed to a computer implemented method for defining a first marker defined biological compartment relative to a second marker defined biological compartment present in a biological sample comprising: a) incubating the sample with a first imaging agent that specifically labels the first marker defined compartment, and a second imaging agent that specifically labels the second marker defined compartment; b) obtaining a first high resolution image of the first imaging agent labeled sample, and a second high resolution image of the second imaging agent labeled sample; c) determining a first and a second imaging agent intensity in each corresponding pixel location in the first and the second image; d) performing a clustering analysis on each pixel based on the first and the second imaging agent intensity of each pixel in each of the pixel to calculate clusters; e) assigning those pixels in the cluster characterized by high first imaging agent pixel intensity and low second imaging agent pixel intensity to the first compartment; f) assigning those pixels in the cluster characterized by high second imaging agent pixel intensity and low first imaging agent pixel intensity to the second compartment; and g) assigning those pixels in the cluster characterized by low first imaging agent pixel intensity and low second imaging agent pixel intensity to background and removing such pixels from further analysis, thereby defining a first marker defined sub-cellular compartment relative to a second marker defined sub-cellular compartment.

In one embodiment, the present invention is directed to a computer implemented method for localizing and quantitating a particular biomarker within a first marker defined biological compartment relative to a second marker defined biological compartment present in a biological sample comprising: a) incubating the tissue sample with a first imaging agent that specifically labels the first marker defined compartment, a second imaging agent that specifically labels a second marker defined sub-cellular compartment, and a third imaging agent that specifically labels the biomarker; b) obtaining a first high resolution image of the first imaging agent labeled sample, a second high resolution image of the second imaging agent labeled sample, and a third high resolution image of the third imaging agent labeled sample; c) determining the first and second imaging agent pixel intensity in each of the pixel locations in the first and the second image; d) performing a clustering analysis on the pixels to assign pixels to the first marker defined compartment or the second marker defined compartment; and e) analyzing in the third image the pixel locations assigned to the compartments so as to identify those pixel locations with an intensity value indicative of the third imaging agent, and determining the total intensity value of the third imaging at the pixel locations assigned to each of the first and second compartments, so as to thereby localize and quantitate the biomarker in the first compartment relative to the second compartment. In a particular embodiment, the high resolution images are obtained using an upright or inverted optical microscope. In a particular embodiment, the cluster analysis is performed using reiterative k-means clustering on the first and the second pixel intensity in each of the pixel locations to calculate three centroids using Euclidean or log-likelihood distances. In a particular embodiment, the methods of the present invention optionally comprise i) plotting the pixel locations and the calculated centroids where the axes of the plot comprise the intensity of the first imaging agent and the intensity of the second imaging agent at pixel locations for the first compartment and the second compartment; ii) connecting the centroids to define a triangle; iii) assigning those pixel locations having an intensity not within the area of the triangle: (1) to the first compartment if the pixel intensity is substantially indicative of the first imaging agent; (2) to the second compartment if the pixel intensity is substantially indicative of the second imaging agent, or (3) to neither compartment if the pixel intensity is substantially indicative of background; and iv) assigning those pixel locations within the area of the triangle the first compartment or the second compartment based upon a value corresponding to the probability that the pixel originates from the first or the second compartment. In a particular embodiment, the biomarker is selected from the group consisting of: a protein, a peptide, a nucleic acid, a lipid and a carbohydrate. In a particular embodiment, each of the first, the second and the third imaging agents comprise a fluorophore. In a particular embodiment, the quantitation of the biomarker present within the first or the second compartment comprises summing the intensity values of the third imaging agent at the pixel locations within the compartment and dividing the sum by the number of pixels in the compartment. In a particular embodiment, a pixel location not assigned to the first or the second compartment is assigned to a third compartment. In a particular embodiment, the sample is a tissue sample with a thickness of about five microns. In a particular embodiment, the first compartment is a cellular membrane and the second compartment is a cell nucleus. In a particular embodiment, the biological sample is a fixed tissue section. In a particular embodiment, the first or the second imaging agent reacts with a marker that is selected from the group consisting of: cytokeratin, beta catenin, alpha catenin and vimentin. In a particular embodiment, at least one of the first, the second or the third imaging agents comprises a fluorophore selected from the group consisting of: 4',6-diamidino-2-phenylindole (DAPI), Cy3, Cy-5-tyramide and Alexa fluor dyes. In a particular embodiment, the biomarker is selected from the group consisting of: Her-2/neu, estrogen receptor, progesterone receptor, epidermal growth factor receptor, phosphatase and tensin homolog (PTEN), and excision repair cross complementation group 1 (ERCC1). In a particular embodiment, a mask is applied to the first, the second and the third high resolution images, and only pixels within the mask are analyzed.

In one embodiment, the present invention is directed to a computer readable medium comprising the computer readable instructions stored thereon for execution by a processor to perform a method for determining an optimal dilution of a reagent for use in a quantitative immunoassay comprising the steps of: receiving a plurality of dilution sets, each dilution set having a different respective dilution value and comprising a respective plurality of immunoassay staining intensity values; determining for each of the plurality of dilution sets a respective dynamic range metric related to the respective plurality of immunoassay staining intensity values; and identifying the dilution set having the numerically greatest dynamic range metric, the dilution value of the identified dilution set being representative of an optimal dilution level of the reagent for use in the quantitative immunoassay.

In one embodiment, the present invention is directed to an electromagnetic signal carrying computer-readable instructions for determining an optimal dilution of a reagent for use in a quantitative immunoassay comprising the steps of: receiving a plurality of dilution sets, each dilution set having a different respective dilution value and comprising a respective plurality of immunoassay staining intensity values; determining for each of the plurality of dilution sets a respective dynamic range metric related to the respective plurality of immunoassay staining intensity values; and identifying the dilution set having the numerically greatest dynamic range metric, the dilution value of the identified dilution set being representative of an optimal dilution level of the reagent for use in the quantitative immunoassay.

In one embodiment, the present invention is directed to a computer implemented method for defining a first marker defined sub-cellular compartment relative to a second marker defined sub-cellular compartment present in individual cells of interest contained in a tissue sample comprising: a) incubating the tissue sample with a first stain that specifically labels the first marker defined sub-cellular compartment, a second stain that specifically labels a second marker defined sub-cellular compartment, b) obtaining a high resolution image of each of the first and the second stain in the tissue sample using a microscope so as to obtain: i) a first image of the first marker defined sub-cellular compartment; ii) a second image of the second marker defined sub-cellular compartment; and c) determining the first and second stain intensity in each of the pixel locations in the first and the second image; d) plotting the pixels, where the axes of the plot comprise the intensity of the first stain and the intensity of the second stain; e) performing reiterative k-means clustering on the first and the second stain intensity in each of the pixel locations to calculate three clusters; f) assigning those pixels in the cluster characterized by high first stain intensity and low second stain intensity to the first compartment; g) assigning those pixels in the cluster characterized by high second stain intensity and low first stain intensity to the second compartment; h) assigning those pixels in the cluster characterized by low first stain intensity and low second stain intensity to background and removing such pixels from further analysis; i) assigning those pixels with first stain intensity and second stain intensity to either the first compartment or the second compartment based upon based on probability thereby defining a first marker defined sub-cellular compartment relative to a second marker defined sub-cellular compartment.

In one embodiment, the present invention is directed to a computer implemented method for defining a first marker defined sub-cellular compartment relative to a second marker defined sub-cellular compartment present in individual cells of interest contained in a tissue sample comprising: a) incubating the tissue sample with a first stain that specifically labels the first marker defined sub-cellular compartment, a second stain that specifically labels a second marker defined sub-cellular compartment, b) obtaining a high resolution image of each of the first and the second stain in the tissue sample using a microscope so as to obtain: i) a first image of the first marker defined sub-cellular compartment; ii) a second image of the second marker defined sub-cellular compartment; and c) determining the first and second stain intensity in each of the pixel locations in the first and the second image; d) plotting the pixels, where the axes of the plot comprise the intensity of the first stain and the intensity of the second stain; e) performing reiterative k-means clustering on the first and the second stain intensity in each of the pixel locations to calculate three clusters; f) assigning those pixels in the cluster characterized by high first stain intensity and low second stain intensity to the first compartment; g) assigning those pixels in the cluster characterized by high second stain intensity and low first stain intensity to the second compartment; h) assigning those pixels in the cluster characterized by low first stain intensity and low second stain intensity to background and removing such pixels from further analysis; i) assigning those pixels with first stain intensity and second stain intensity to neither the first compartment or the second compartment; thereby defining a first marker defined sub-cellular compartment relative to a second marker defined sub-cellular compartment.

In one embodiment, the present invention is directed to a computer implemented method for localizing and quantitating a particular biomarker within a first marker defined sub-cellular compartment relative to a second marker defined sub-cellular compartment present in individual cells of interest contained in a tissue sample comprising: a) incubating the tissue sample with a first stain that specifically labels the first marker defined sub-cellular compartment, a second stain that specifically labels a second marker defined sub-cellular compartment, and a third stain that specifically labels the biomarker; b) obtaining a high resolution image of each of the first, the second, and the third stain in the tissue sample using an upright or inverted optical microscope so as to obtain: i) a first image of the first marker defined sub-cellular compartment; ii) a second image of the second marker defined sub-cellular compartment; and iii) a third image of the biomarker, c) determining the first and second stain intensity in each of the pixel locations in the first and the second image; d) performing reiterative k-means clustering on the first and the second stain intensity in each of the pixel locations to assign pixels to the first marker defined sub-cellular compartment of the second marker defined sub-cellular compartment; e) analyzing in the third image the pixel locations assigned to the first sub-cellular compartment, the second sub-cellular compartment, or both compartments in step (f) and step (g) so as to identify those pixel locations having an intensity value indicative of the third stain, and determining the total intensity value of the third stain at the pixel locations assigned to each of the first and second sub-cellular compartment; so as to thereby localize and quantitate the biomarker in the first sub-cellular compartment relative to the second sub-cellular compartment In one embodiment, the present invention is directed to a computer implemented method for localizing and quantitating a particular biomarker within a first marker defined sub-cellular compartment relative to a second marker defined sub-cellular compartment present in individual cells of interest contained in a tissue sample comprising: a) incubating the tissue sample with a first stain that specifically labels the first marker defined sub-cellular compartment, a second stain that specifically labels a second marker defined sub-cellular compartment, and a third stain that specifically labels the biomarker; b) obtaining a high resolution image of each of the first, the second, and the third stain in the tissue sample using an upright or inverted optical microscope so as to obtain: i) a first image of the first marker defined sub-cellular compartment; ii) a second image of the second marker defined sub-cellular compartment; and iii) a third image of the biomarker, c) determining the first and second stain intensity in each of the pixel locations in the first and the second image; d) performing reiterative k-means clustering on the first and the second stain intensity in each of the pixel locations to calculate three centroids using Euclidean or log-likelihood distances; e) plotting the pixel locations and the calculated centroids where the axes of the plot comprise the intensity of the first stain and the intensity of the second stain pixel locations for the first compartment and the second compartment. f) connecting the centroids to define a triangle, g) assigning those pixel locations having an intensity not within the area of the triangle: (1) to the first compartment if the pixel intensity is substantially indicative of the first stain; (2) to the second compartment if the pixel intensity is substantially indicative of the second stain, or (3) to neither compartment if the pixel intensity is substantially indicative of background; h) assigning those pixel locations within the area of the triangle the first compartment or the second compartment based upon a value corresponding to the probability that the pixel originates from the first or the second compartment; i) analyzing in the third image the pixel locations assigned to the first sub-cellular compartment, the second sub-cellular compartment, so as to identify those pixel locations having an intensity value indicative of the third stain, and determining the total intensity value of the third stain at the pixel locations assigned to each of the first and second sub-cellular compartment; so as to thereby localize and quantitate the biomarker in the first sub-cellular compartment relative to the second sub-cellular compartment.

Other features, objects, and advantages of the invention will be apparent from the following figures, detailed description and claims.

BRIEF DESCRIPTION OF THE DRAWINGS

FIG. 9A) Model description of C-AQUA method showing specific pixel assignment: background (box between points A and C), 100% cytoplasm/Cy3 (box between the left border and C; Y-axis; 0% nuclear/DAPI), 0-100% cytoplasm/Cy3 (triangle ABC; 0% nuclear/DAPI), 0-100% nuclear/DAPI (triangle ABD, 0% cytoplasm/Cy3), and 100% nuclear/DAPI (bottom box; X-axis; 0% cytoplasm/Cy3). FIG. 9B) 2×2 scatter-plot showing Cy3 (Y) and Dapi (X) pixel intensities graphed against one another with indicated centroids (B, Background; C, Cytoplasm; N, Nuclear). This image passed validation in that both compartment centroids were greater than 1 standard deviation away from the background centroid. FIG. 9C) 2×2 scatter-plot of a different tissue spot showing indicated pixel intensities and centroids. This image failed validation due to insufficient distance (<1 standard deviation) between the cytoplasmic centroid (C) and background centroid (B).

FIG. 10A) Regression analysis with indicated Pearson R and Spearman's Rho values between AQUA® scores generated by two highly trained operators using traditional AQUA® analysis algorithms. FIG. 10B) Regression analysis with indicated Pearson R and Spearman's Rho values between AQUA® scores generated by two highly trained operators using C-AQUA algorithms on the same data set as in A.

FIG. 11A) Linear regression analysis for nuclear compartment size between AQUA® analysis (Y-axis) and C-AQUA analysis (X-axis) with indicated Pearson's R and Spearman's Rho values. FIG. 11B) Linear regression analysis for cytoplasmic compartment size between AQUA® analysis (Y-axis) and C-AQUA analysis (X-axis) with indicated Pearson's R and Spearman's Rho values.

FIG. 12A) Linear regression analysis for ER AQUA® scores between AQUA® analysis (Y-axis) and C-AQUA analysis (X-axis) with indicated Pearson's R and Spearman's Rho values. FIG. 12B) Linear regression analysis for PR AQUA® scores between AQUA® analysis (Y-axis) and C-AQUA analysis (X-axis) with indicated Pearson's R and Spearman's Rho values. FIG. 12C) Linear regression analysis for Her2 AQUA® scores between AQUA® analysis (Y-axis) and C-AQUA analysis (X-axis) with indicated Pearson's R and Spearman's Rho values.

FIG. 13B) traditional AQUA®: 12.4% reduction in overall survival (log-rank p=0.021) from 84.2% (PR High) to 71.8% (PR Low); C-AQUA: 14.5% reduction in overall survival (log-rank p=0.001) from 83.3% (PR High) to 68.8% (PR Low); and FIG. 13C) traditional AQUA®: 18.5% total reduction in overall survival (log-rank p=0.022) from 77.1% (Her2 Low) to 73.8% (Her2 Mid) to 58.6% (Her2 High); C-AQUA: 24.2% total reduction in overall survival (log-rank p=0.002) from 77.8% (Her2 Low) to 73.8% (Her2 Mid) to 53.6% (Her2 High)].

FIG. 14A) Linear regression analysis for nuclear PTEN expression as determined by AQUA® analysis (Y-axis) and C-AQUA analysis (X-axis) with indicated Pearson's R. FIG. 14B) Linear regression analysis for cytoplasmic PTEN expression as determined by AQUA® analysis (Y-axis) and C-AQUA analysis (X-axis) with indicated Pearson's R values.

FIG. 14A) Linear regression analysis for nuclear ERCC1 expression as determined by AQUA® analysis (Y-axis) and C-AQUA analysis (X-axis) with indicated Pearson's R. FIG. 14B) Linear regression analysis for cytoplasmic ERCC1 expression as determined by AQUA® analysis (Y-axis) and C-AQUA analysis (X-axis) with indicated Pearson's R values.

DETAILED DESCRIPTION

Figure 1:
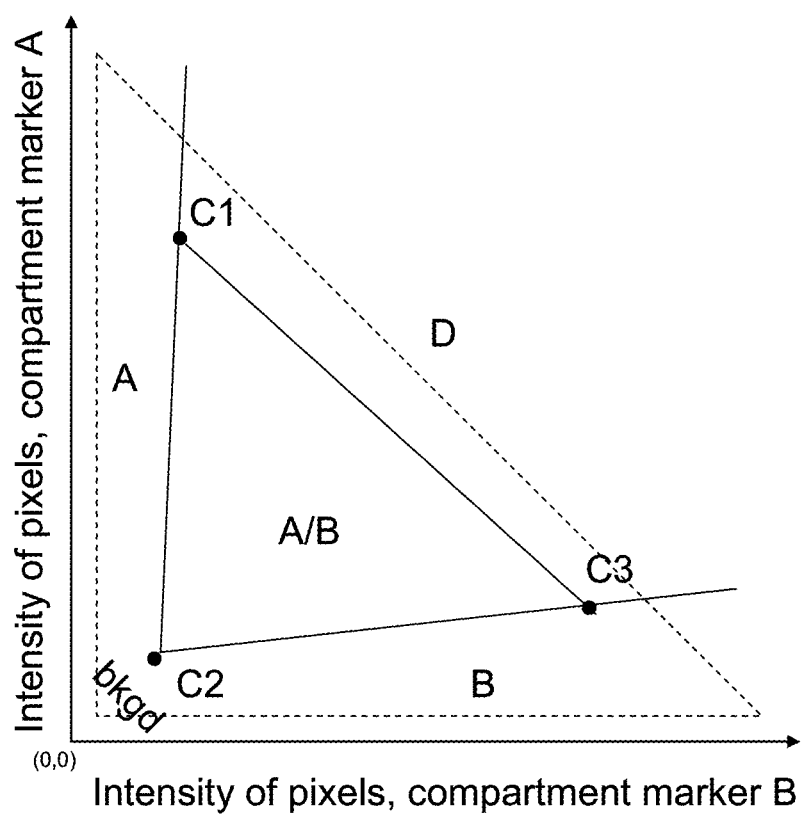
FIG. 1 is a schematic of the clustering used to determine three centroids in the data.

It is to be appreciated that certain aspects, modes, embodiments, variations and features of the invention are described below in various levels of detail to provide a substantial understanding of the present invention.

Unless defined otherwise, all technical and scientific terms used herein generally have the same meaning as commonly understood by one of ordinary skill in the art to which this invention belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell biology, immunohistochemistry, and imaging (e.g., cells and tissue) described below are those well known and commonly employed in the art. Standard techniques, or modifications thereof, are used for immunohistochemical analyses. All references cited herein are incorporated herein by reference in their entireties and for all purposes to the same extent as if each individual publication, patent, or patent application was specifically and individually incorporated by reference in its entirety for all purposes.

Tissue microarray technology offers the opportunity for high throughput analysis of tissue samples (Konen, J. et al., Nat. Med. 4:844-7 (1998); Kallioniemi, O. P. et al., Hum. Mol. Genet. 10:657-62 (2001); Rimm, D. L. et al., Cancer J. 7:24-31 (2001)). For example, the ability to rapidly perform large scale studies using tissue microarrays can provide critical information for identifying and validating drug targets/prognostic markers (e.g. estrogen receptor (ER) and HER2/neu) and candidate therapeutics.

Most biomarkers exhibit a parametric (normal, "bell-shaped") distribution, and consequently are best analyzed by a continuous scale (e.g., 0 to 1000). Unfortunately, manual observation tends to be nominal (e.g. 1+, 2+, 3+), primarily because the human eye in unable to reliably distinguish subtle differences in staining intensity. Several methods have been developed to translate nominal manual observations into a continuous scale. Foremost among these is the H-score where the percent of positively stained cells (0 to 100) is multiplied by the staining intensity (e.g. 0 to 3) to make a theoretically continuous scale (0 to 300). However, the inability to detect subtle differences in staining intensity, particularly at the low and high ends of the scale, as well as the tendency to round scores (e.g. 50% at 3+ for a score of 150, versus 47% at 3+ for a score of 141), limits the effectiveness of the H-score.

In some aspects, the present invention provides improved methods to quantify and localize a particular target in defined cellular components. The present inventors have discovered a method to accomplish this that has the advantage of being completely objective and minimizes operator intervention or decision making. The method performs a clustering on the intensity data for each cellular compartment acquired. This clustering allows for removal of background, assignment of specific pixels to a given compartment and probabilistic assignment of pixels to each compartment where there may be overlapping signals. Once pixels are assigned to each compartment (or discarded in the case of noise) the associated target signals can be measured, for example summed and a score calculated.

The invention provides methods for objective pixel assignment to specific compartments. The assignment is preferentially determined on an image-to-image basis, rather than setting universal criteria. Furthermore, pixel assignment (e.g., Cy3/Cytokeratin pixels to cytoplasm) is also a function of other compartment images such that consideration is given to the status of pixels in other compartment images. In one embodiment one image is of a first stain that specifically labels a first compartment (e.g., a Cy3/cytokeratin image, representing the cytoplasmic compartment) and a second image is of a second stain that specifically labels a second compartment (e.g., DAPI image, representing the nuclear compartment) and pixel assignments are based on four criteria:

1.) Low intensity in both first and second image (e.g., DAPI and Cy3):BACKGROUND: REMOVE 2.) High second stain (e.g., DAPI) intensity relative to first stain (Cy3) intensity: SECOND COMPARTMENT (e.g., NUCLEAR)

3.) High first stain (e.g., Cy3) intensity relative to second stain (e.g., DAPI) intensity: FIRST COMPARTMENT (e.g., CYTOPLASMIC)

4.) High second stain and first stain (e.g., DAPI and Cy3) intensity: INDETERMINANT: REMOVE Clustering is a mathematical algorithmic function whereby centroids within data sets are defined by relative distances of each data point to one another, as determined, for example, by Euclidean or log-likelihood distance. While not wishing to be bound by theory, it is believed that clustering pixel intensities from at least two images (i.e. DAPI and Cy3), could result in centroids that define pixels as described, at least, by the above criteria. Because clustering is objective and can be performed individually on each image, clustering was discovered to provide reliable assignment of pixels to compartments, independent of operator intervention.

In another embodiment, pixels containing signal indicative of both the first and second stain are assigned to compartments by the following method. Every pixel in acquired images has three attributes—intensity contribution from compartment marker A, intensity contribution from compartment marker B and an intensity contribution from the target or biomarker of interest. These intensities are measured in their respective fluorescence channels per the experimental configuration. To avoid experimental bias, the target intensity is not manipulated in this current method. Thus, the data for the two compartment attributes can be illustrated in a two-dimensional plot schematically shown in FIG. 1. The typical spread of the data is represented by the dashed right triangle.

Pixels with a strong bias towards either of the axes can be assigned to that compartment (e.g., pixels in regions A and B could be absolutely assigned to compartments A and B respectively). Pixels near the origin represent low intensities for both channels and can be discarded as background along with outlier pixels that have high intensity but similar values, shown in region D. Pixels that remain in the region labeled A/B can then be assigned to each compartment based on probability. This assignment allows target signal in those pixels to be distributed across both compartments based on the probability characterization.

To define the regions described above, for example, for every image, clustering is used to determine three centroids in the data (shown as C1, C2 and C3). This method is fully automated and does not require any operator decisions to proceed. The analysis is accomplished by performing k-means clustering on three centroids using Euclidean distances. Once these points are determined, the regions illustrated in the FIG. 1 are generated using these points. The data are then analyzed as follows: (i) Background and outlier pixels are discarded from further calculation. A pixel is defined as background if its distance to the origin is less than twice that of the background centroid (C2) distance to the origin. A pixel is define as an outlier if its intensity exceeds the value defines by the line or plane defined by the outermost centroids (e.g., C1 and C3 in FIG. 1; region D); (ii) Pixels in regions A and B are assigned exclusively to those two compartments; (iii) Pixels in the triangular region A/B are then assigned a probability value that allows them to essentially be distributed in multiple compartments. This probability value can be calculated based on distance from the two regions A and B, or, using a shape function that will also assign a probability of each pixel having a contribution from the background region by examining each pixel's distance from the three vertices given by the centroids; (iv) With all pixels assigned, the associated target scores can be summed up for each compartment and a score calculated using standard methods:

$$\frac{\sum_{i}^{\# pixels} Int_i * P_i}{\sum_{i}^{\# pixels} P_i}$$

where Int is the intensity of the pixel, P is the probability of the pixel being assigned to a particular compartment (ranging from 0 to 1).

General Methods

In general, described herein are a collection of techniques that can be used for rapid, automated analysis of cell containing samples, including tissues and tissue microarrays. While these techniques build on one another and are described as a cohesive process, each technique has wide applicability and may be used individually or in combinations other than those described below.

In a particular embodiment, the methods of the invention are preferentially used with AQUA® analysis, the features of which are described in U.S. Pat. No. 7,219,016, which is incorporated by reference in its entirety.

In a typical AQUA® experimental setup, tissue samples are stained with markers that define, for example, the sub-cellular compartments of interest and the specific target (or targets) being studied. Pixel-based local assignment for compartmentalization of expression (PLACE) is the key algorithm that functions to effectively segment image pixels for the purpose of expression compartmentalization. A critical step in this algorithm is the setting of intensity thresholds that are used to delineate background or non-specific pixels from signal-specific pixels. Images that have been "masked" in this way are subsequently combined in a mutually-exclusive fashion such that pixels above the thresholds are assigned to specific sub-cellular compartments. Once pixels have been assigned to each compartment, the signal for the target biomarker can then be averaged over all of the pixels assigned to a given compartment, which is the AQUA® score for that sample.

For example, in an epithelial tumor specimen, two stains can be used to differentiate the tumor region and incorporated sub-cellular compartments: DAPI (4'-6-Diamidino-2-phenylindole; a nuclear/dsDNA specific staining marker) and cytokeratin (an epithelial specific biomarker tagged for fluorescent readout). These images are individually thresholded to remove non-specific signal then combined to produce an image that represents pixels that are not only epithelial specific but also represent cytoplasm and nuclear-specific pixels. Pixel intensities from a specific target that has been labeled for readout in a third fluorescent channel can subsequently be quantified within this "PLACEd" image.

It would be advantageous, specifically for clinical operation, to enhance the AQUA® analysis scoring algorithm such that image segmentation is completely automated, thus removing the user-defined threshold step. This would improve the system in several ways: First, due to operator time associated with defining an optimized threshold setting, efficiency of the system would greatly increase. Second, due to the subjective nature of setting thresholds, even by experienced operators, operator-to-operator variability could be removed. Third, for purposes of clinical and/or research lab efficiency and quality control, a uniform method of setting thresholds must be applied for all channel-specific images acquired across a TMA cohort or whole tissue section. Development of an automated PLACE-like method would allow for image segmentation to be optimized on an image-by-image basis. And finally, the method described here involves examination of compartment images simultaneously, so thresholds are set in the context of pixel data for all compartment markers.

The present invention may be used to localize and quantitate a biomarker within any imageable, cell-containing sample, including, but not limited to, tissue biopsies and cell containing fluid samples, such as, for example, blood, urine, spinal fluid, saliva, lymph, pleural fluid, peritoneal fluid and pericardial fluid and for the analysis of tissue microarrays.

Any optical or non-optical imaging device can be used, such as, for example, upright or inverted optical microscopes, scanning confocal microscopes, cameras, scanning or tunneling electron microscopes, scanning probe microscopes, and imaging infrared detectors etc.

In the embodiments described above, the computer can include hardware, software, or a combination of both to control the other components of the system and to analyze the images. The analysis described above is implemented in computer programs using standard programming techniques. Such programs are designed to execute on programmable computers each comprising a processor, a data storage system (including memory and/or storage elements), at least one input device, at least one output device, such as a display or printer. The program code is applied to input data (e.g., stitched together images or image stacks) to perform the functions described herein and generate information (e.g., localization of signal), which is applied to one or more output devices. Each computer program can be implemented in a high-level procedural or object-oriented programming language, or an assembly or machine language. Each such computer program can be stored on a computer readable storage medium (e.g., CD ROM or magnetic diskette) that, when read by a computer, can cause the processor in the computer to perform the analysis described herein.

The following provides a detailed description of a specific embodiment of the preparation and analysis of tissue microarrays according to methods described herein, although similar steps could be performed with respect to any cell containing sample. A tissue microarray includes multiple samples of histospots prepared from histocores embedded typically in a thin block of paraffin at regular intervals, forming a series of rows and columns. Histospots (thin sections of histocores) may be substantially disk-like in shape and will typically a thickness of about five microns and a diameter of about 0.6 millimeters. Typically the centers of the histospots are spaced about a few tenths of a millimeter apart in paraffin blocks. Sections of the histospots may be mounted on a microscope slide. A tissue microarray may include any number of histospots, typically on the order of several hundred to a few thousand.

An optical microscopy station can be used to obtain an appropriate image of the tissue. A microscopy station includes an optical microscope for imaging the tissue, and a computer for analyzing the images. An optical microscope includes a mount, housing a light source, a sample stage, an objective lens and a CCD camera. A frame grabber software is used to acquire the images through CCD camera.

An optical microscope also includes several light filters to provide the appropriate illumination spectra for standard or fluorescent microscopy. For example, for fluorescent microscopy the filters may be in filter wheels and a housing, which house a series of dichroic filters. The filters in the wheel allow selection of the appropriate illumination spectra. The filters in wheel alter (filter) the transmitted light for isolation of spectral signatures in fluorescent microscopy. A sample stage supports and appropriately positions the microscope slide containing the tissue sample or tissue microarray. A sample stage can be linearly translated in the x, y, and z directions (axes are shown). A sample stage includes motors to enable automated translation. A computer controls the sample stage translation by servo control of the motors.

A tissue microarray can be imaged as follows: a user places the microarray on a sample stage. The user adjusts the sample stage so that the first (e.g., top-left) histospot is at the center of the field of view and focused on by the CCD camera. The objective lens should be adjusted to the appropriate resolution, for example, a 0.6 millimeter histospot can be viewed at 10× magnification. The histospots generally correspond to areas of higher light intensity than the surrounding paraffin, as assessed through various means including signals derived from the visible light scattering of stained tissues, tissue autofluorescence or from a fluorescent tag. A computer can acquire a low-resolution image (e.g. 64 pixel×64 pixel with 16 bit resolution) using computer software (Softworx 2.5, Applied Precision, Issaquah, Wash.) and an imaging platform (e.g., Deltavision). A computer automatically translates sample stage by an amount approximately equal to a field of view. The computer then acquires a second low-resolution image. This process is repeated until the computer has acquired images of the entire tissue sample or microarray. Using commercially available software, the computer then generates a composite image of the entire tissue microarray by stitching together the sequence of images like patchwork.

Biological markers, which may be detected in accordance with the present invention include, but are not limited to any nucleic acids, proteins, peptides, lipids, carbohydrates or other components of a cell. Certain markers are characteristic of particular cells, while other markers have been identified as being associated with a particular disease or condition. Examples of known prognostic markers include enzymatic markers such as, for example, galactosyl transferase II, neuron specific enolase, proton ATPase-2, and acid phosphatase. Hormone or hormone receptor markers include human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, and insulin receptor.

Lymphoid markers include alpha-1-antichymotrypsin, alpha-1-antitrypsin, B cell marker, bcl-2, bcl-6, B lymphocyte antigen 36 kD, BM1 (myeloid marker), BM2 (myeloid marker), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage marker, muramidase (lysozyme), p80 anaplastic lymphoma kinase, plasma cell marker, secretory leukocyte protease inhibitor, T cell antigen receptor (JOVI 1), T cell antigen receptor (JOVI 3), terminal deoxynucleotidyl transferase, unclustered B cell marker.

Tumor markers include alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumour associated mucin antigen), chromogranin A, clusterin (apolipoprotein J), epithelial membrane antigen, epithelial-related antigen, epithelial specific antigen, epidermal growth factor receptor, estrogen receptor, gross cystic disease fluid protein-15, hepatocyte specific antigen, HER2, heregulin, human gastric mucin, human milk fat globule, MAGE-1, matrix metalloproteinases, melan A, melanoma marker (HMB45), mesothelin, metallothionein, microphthalmia transcription factor (MITF), Muc-1 core glycoprotein. Muc-1 glycoprotein, Muc-2 glycoprotein, Muc-5AC glycoprotein, Muc-6 glycoprotein, myeloperoxidase, Myf-3 (Rhabdomyosarcoma marker), Myf-4 (Rhabdomyosarcoma marker), MyoD1 (Rhabdomyosarcoma marker), myoglobin, nm23 protein, placental alkaline phosphatase, prealbumin, progesterone receptor, prostate specific antigen, prostatic acid phosphatase, prostatic inhibin peptide, PTEN, renal cell carcinoma marker, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, von Willebrand factor, CD34, CD34, Class II, CD51 Ab-1, CD63, CD69, Chk1, Chk2, claspin C-met, COX6C, CREB, Cyclin D1, Cytokeratin, Cytokeratin 8, DAPI, Desmin, DHP (1-6 Dipheynyl-1,3,5-Hexatriene), E-Cadherin, EEA1, EGFR, EGFRvIII, EMA (Epithelial Membrane Antigen), ER, ERB3, ERCC1, ERK, E-Selectin, FAK, Fibronectin, FOXP3, Gamma-H2AX, GB3, GFAP, Giantin, GM130, Golgin 97, GRB2, GRP78BiP, GSK3 Beta, HER-2, Histone 3, Histone 3_K14-Ace [Anti-acetyl-Histone H3 (Lys 14)], Histone 3_K18-Ace [Histone H3-Acetyl Lys 18), Histone 3_K27-TriMe, [Histone H3 (trimethyl K27)], Histone 3_K4-diMe [Anti-dimethyl-Histone H3 (Lys 4)], Histone 3_K9-Ace [Acetyl-Histone H3 (Lys 9)], Histone 3_K9-triMe [Histone 3-trimethyl Lys 9], Histone 3_S10-Phos [Anti-Phospho Histone H3 (Ser 10), Mitosis Marker], Histone 4, Histone H2A.X_S139-Phos [Phospho Histone H2A.X (Ser139)antibody], Histone H2B, Histone H3_DiMethyl K4, Histone H4_TriMethyl K20-Chip grad, HSP70, Urokinase, VEGF R1, ICAM-1, IGF-1, IGF-1R, IGF-1 Receptor Beta, IGF-II, IGF-IIR, IKB-Alpha IKKE, IL6, IL8, Integrin alpha V beta 3, Integrin alpha V beta6, Integrin Alpha V/CD51, integrin B5, integrin B6, Integrin B8, Integrin Beta 1(CD 29), Integrin beta 3, Integrin beta 5 integrinB6, IRS-1, Jagged 1, Anti-protein kinase C Beta2, LAMP-1, Light Chain Ab-4 (Cocktail), Lambda Light Chain, kappa light chain, M6P, Mach 2, MAPKAPK-2, MEK 1, MEK 1/2 (Ps222), MEK 2, MEK1/2 (47E6), MEK1/2 Blocking Peptide, MET/HGFR, MGMT, Mitochondrial Antigen, Mitotracker Green FM, MMP-2, MMP9, E-cadherin, mTOR, ATPase, N-Cadherin, Nephrin, NFKB, NFKB p105/p50, NF-KB P65, Notch 1, Notch 2, Notch 3, OxPhos Complex IV, p130Cas, p38 MAPK, p44/42 MAPK antibody, P504S, P53, P70, P70 S6K, Pan Cadherin, Paxillin, P-Cadherin, PDI, pEGFR, Phospho AKT, Phospho CREB, phospho EGF Receptor, Phospho GSK3 Beta, Phospho H3, Phospho HSP- 70, Phospho MAPKAPK-2, Phospho MEK1/2, phospho p38 MAP Kinase, Phospho p44/42 MAPK, Phospho p53, Phospho PKC, Phospho S6 Ribosomal Protein, Phospho Src, phospho-Akt, Phospho-Bad, Phospho-IKB-a, phospho-mTOR, Phospho-NF-kappaB p65, Phospho-p38, Phospho-p44/42 MAPK, Phospho-p70 S6 Kinase, Phospho-Rb, phospho-Smad2, PIM1, PIM2, PKC β, Podocalyxin, PR, PTEN, R1, Rb 4H1, R-Cadherin, ribonucleotide Reductase, RRM1, RRM11, SLC7A5, NDRG, HTF9C, HTF9C, CEACAM, p33, S6 Ribosomal Protein, Src, Survivin, Synapopodin, Syndecan 4, Talin, Tensin, Thymidylate Synthase, Tuberlin, VCAM-1, VEGF, Vimentin, Agglutinin, YES, ZAP-70 and ZEB.

Cell cycle associated markers include apoptosis protease activating factor-1, bcl-w, bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mc1-1, minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, topoisomerase II beta.

Neural tissue and tumour markers include alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma marker, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, serotonin, SNAP-25, synapsin I, synaptophysin, tau, tryptophan hydroxylase, tyrosine hydroxylase, ubiquitin.

Cluster differentiation markers include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CD137, CD138, CD139, CD140a, CD140b, CD141, CD142, CD143, CD144, CDw145, CD146, CD147, CD148, CDw149, CD150, CD151, CD152, CD153, CD154, CD155, CD156, CD157, CD158a, CD158b, CD161, CD162, CD163, CD164, CD165, CD166, and TCR-zeta.

Other cellular markers include centromere protein-F (CENP-F), giantin, involucrin, lamin A&C [XB 10], LAP-70, mucin, nuclear pore complex proteins, p180 lamellar body protein, ran, r, cathepsin D, Ps2 protein, Her2-neu, P53, S100, epithelial marker antigen (EMA), TdT, MB2, MB3, PCNA, and Ki67.

Cell containing samples may be stained using dyes or stains, histochemicals, or immunohistochemicals that directly react with the specific biomarkers or with various types of cells or sub-cellular compartments. Not all stains are compatible. Therefore the type of stains employed and their sequence of application should be well considered, but can be readily determined by one of skill in the art. Such histochemicals may be chromophores detectable by transmittance microscopy or fluorophores detectable by fluorescence microscopy. In general, cell containing samples may be incubated with a solution comprising at least one histochemical, which will directly react with or bind to chemical groups of the target. Some histochemicals must be co-incubated with a mordant or metal to allow staining A cell containing sample may be incubated with a mixture of at least one histochemical that stains a component of interest and another histochemical that acts as a counterstain and binds a region outside the component of interest. Alternatively, mixtures of multiple probes may be used in the staining, and provide a way to identify the positions of specific probes.

The following, non-limiting list provides exemplary chromophores that may be used as histological imaging agents (stains or counterstains) and their target cells, sub-cellular compartments, or cellular components: Eosin (alkaline cellular components, cytoplasm), Hematoxylin (nucleic acids), Orange G (red blood, pancreas, and pituitary cells), Light Green SF (collagen), Romanowsky-Giemsa (overall cell morphology), May-Grunwald (blood cells), Blue Counterstain (Trevigen), Ethyl Green (CAS) (amyloid), Feulgen-Naphthol Yellow S (DNA), Giemsa (differentially stains various cellular compartments), Methyl Green (amyloid), pyronin (nucleic acids), Naphthol-Yellow (red blood cells), Neutral Red (nuclei), Papanicolaou stain (which typically includes a mixture of Hematoxylin, Eosin Y, Orange G and Bismarck Brown mixture (overall cell morphology), Red Counterstain B (Trevigen), Red Counterstain C (Trevigen), Sirius Red (amyloid), Feulgen reagent (pararosanilin) (DNA), Gallocyanin chrom-alum (DNA), Gallocyanin chrom-alum and Naphthol Yellow S (DNA), Methyl Green-Pyronin Y (DNA), Thionin-Feulgen reagent (DNA), Acridine Orange (DNA), Methylene Blue (RNA and DNA), Toluidine Blue (RNA and DNA), Alcian blue (carbohydrates), Ruthenium Red (carbohydrates), Sudan Black (lipids), Sudan IV (lipids), Oil Red-O (lipids), Van Gieson's trichrome stain (acid fuchsin and picric acid mixture) (muscle cells), Masson trichrome stain (hematoxylin, acid fuchsin, and Light Green mixture) (stains collagen, cytoplasm, nucleioli differently), Aldehyde Fuchsin (elastin fibers), and Weigert stain (differentiates reticular and collagenous fibers). A comprehensive list of such stains, their description, and general use is given in R. D. Lillie, "Conn's Biological Stains", 8th ed., Williams and Wilkins Company, Baltimore, Md. (1969). Suitable mordants and compositions of the preceding are well-known to one of skill in the art.

The following, non-limiting list provides exemplary fluorescent histological stains and their target cells, sub-cellular compartments, or cellular components if applicable: 4',6-diamidino-2-phenylindole (DAPI) (nucleic acids), Eosin (alkaline cellular components, cytoplasm), Hoechst 33258 and Hoechst 33342 (two bisbenzimides) (nucleic acids), Propidium Iodide (nucleic acids), Spectrum Orange (nucleic acids), Spectrum Green (nucleic acids), Quinacrine (nucleic acids), Fluorescein-phalloidin (actin fibers), Chromomycin A 3 (nucleic acids), Acriflavine-Feulgen reaction (nucleic acid), Auramine O-Feulgen reaction (nucleic acids), Ethidium Bromide (nucleic acids). Nissl stains (neurons), high affinity DNA fluorophores such as POPO, BOBO, YOYO and TOTO and others, and Green Fluorescent Protein fused to DNA binding protein, such as histones, ACMA, Quinacrine and Acridine Orange.

A wide variety of proprietary fluorescent organelle-specific probes are commercially available, and include mitochondria-specific probes (MitoFluor and MitoTracker dyes), endoplasmic reticulum (ER) and Golgi probes (ER-Tracker and various ceramide conjugates), and lysosomal probes (LysoTracker dyes). These probes, as well as many nonproprietary fluorescent histochemicals, are available from and extensively described in the Handbook of Fluorescent Probes and Research Products 8.sup.th Ed. (2001), available from Molecular Probes, Eugene, Oreg.

Each cell containing sample may be co-incubated with appropriate substrates for an enzyme that is a cellular component of interest and appropriate reagents that yield colored precipitates at the sites of enzyme activity. Such enzyme histochemical stains are specific for the particular target enzyme. Staining with enzyme histochemical stains may be used to define a sub-cellular component or a particular type of cell. Alternatively, enzyme histochemical stains may be used diagnostically to quantitate the amount of enzyme activity in cells. A wide variety of enzymatic substrates and detection assays are known and described in the art.

Acid phosphatases may be detected through several methods. In the Gomori method for acid phophatase, a cell preparation is incubated with glycerophosphate and lead nitrate. The enzyme liberates phosphate, which combines with lead to produce lead phosphate, a colorless precipitate. The tissue is then immersed in a solution of ammonium sulfide, which reacts with lead phosphate to form lead sulfide, a black precipitate. Alternatively, cells may be incubated with a solution comprising pararosanilin-HCl, sodium nitrite, napthol ASB1 phosphate (substrate), and veronal acetate buffer. This method produces a red precipitate in the areas of acid phosphatase activity. Owing to their characteristic content of acid phosphatase, lysosomes can be distinguished from other cytoplasmic granules and organelles through the use of this assay.

Dehydrogenases may be localized by incubating cells with an appropriate substrate for the species of dehydrogenase and tetrazole. The enzyme transfers hydrogen ions from the substrate to tetrazole, reducing tetrazole to formazan, a dark precipitate. For example, NADH dehydrogenase is a component of complex I of the respiratory chain and is localized predominantly to the mitochondria.

Other enzymes for which well-known staining techniques have been developed, and their primary cellular locations or activities, include but are not limited to the following: ATPases (muscle fibers), succinate dehydrogenases (mitochondria), cytochrome c oxidases (mitochondria), phosphorylases (mitochondria), phosphofructokinases (mitochondria), acetyl cholinesterases (nerve cells), lactases (small intestine), leucine aminopeptidases (liver cells), myodenylate deaminases (muscle cells), NADH diaphorases (erythrocytes), and sucrases (small intestine).

Immunohistochemistry is among the most sensitive and specific histochemical techniques. Each histospot may be combined with a labeled binding composition comprising a specifically binding probe. Various labels may be employed, such as fluorophores, or enzymes that produce a product that absorbs light or fluoresces. A wide variety of labels are known that provide for strong signals in relation to a single binding event. Multiple probes used in the staining may be labeled with more than one distinguishable fluorescent label. These color differences provide a way to identify the positions of specific probes. The method of preparing conjugates of fluorophores and proteins, such as antibodies, is extensively described in the literature and does not require exemplification here.

Although there are at least 120,000 commercially available antibodies, exemplary primary antibodies, which are known to specifically bind cellular components and are presently employed as components in immunohistochemical stains used for research and, in limited cases, for diagnosis of various diseases, include, for example, anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multidrug resistance), anti-CEA antibody (carcinoembryonic antigen), anti-retinoblastoma protein (Rb) antibody, anti-ras oneoprotein (p21) antibody, anti-Lewis X (also called CD15) antibody, anti-Ki-67 antibody (cellular proliferation), anti-PCNA (multiple cancers) antibody, anti-CD3 antibody (T-cells), anti-CD4 antibody (helper T cells), anti-CD5 antibody (T cells), anti-CD7 antibody (thymocytes, immature T cells, NK killer cells), anti-CD 8 antibody (suppressor T cells), anti-CD9/p24 antibody (ALL), anti-CD10 (also called CALLA) antibody (common acute lymphoblasic leukemia), anti-CD11c antibody (Monocytes, granulocytes, AML), anti-CD13 antibody (myelomonocytic cells, AML), anti-CD 14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD41 antibody (platelets, megakaryocytes), anti-LCA/CD45 antibody (leukocyte common antigen), anti-CD45RO antibody (helper, inducer T cells), anti-CD 45RA antibody (B cells), anti-CD39, CD100 antibody, anti-CD95/Fas antibody (apoptosis), anti-CD99 antibody (Ewings Sarcoma marker, MIC2 gene product), anti-CD 106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salvary, glial cells), anti-tau antigen antibody (Alzheimer's disease), anti-fibrin antibody (epithelial cells), anti-keratins antibody, anti-cytokeratin antibody (tumor), anti-alpha-catenin (cell membrane), anti-Tn-antigen antibody (colon carcinoma, adenocarcinomas, and pancreatic cancer); anti-1,8-ANS (1-Anilino Naphthalene-8-Sulphonic Acid) antibody; anti- C4 antibody; anti-2C4 CASP Grade antibody; anti-2C4 CASP a antibody; anti-HER-2 antibody; anti-Alpha B Crystallin antibody; anti-Alpha Galactosidase A antibody; anti-alpha-Catenin antibody; anti-human VEGF R1 (Flt-1) antibody; anti-integrin B5 antibody; anti-integrin beta 6 antibody; anti-phospho-SRC antibody; anti-Bak antibody; anti-BCL-2 antibody; anti-BCL-6 antibody; anti-Beta Catanin antibody; anti-Beta Catenin antibody; anti-Integrin alpha V beta 3 antibody; anti-c ErbB-2 Ab-12 antibody; anti-Calnexin antibody; anti-Calreticulin antibody; anti-Calreticulin antibody; anti-CAM5.2 (Anti-Cytokeratin Low mol. Wt.) antibody; anti-Cardiotin (R2G) antibody; anti-Cathepsin D antibody; Chicken polyclonal antibody to Galactosidase alpha; anti-c-Met antibody; anti-CREB antibody; anti-COX6C antibody; anti-Cyclin D1 Ab-4 antibody; anti-Cytokeratin antibody; anti-Desmin antibody; anti-DHP (1-6 Dipheynyl-1,3,5-Hexatriene) antibody; DSB-X Biotin Goat Anti Chicken antibody; anti-E-Cadherin antibody; anti-EEA1 antibody; anti-EGFR antibody; anti-EMA (Epithelial Membrane Antigen) antibody; anti-ER (Estrogen Receptor) antibody; anti-ERB3 antibody; anti-ERCC1 ERK (Pan ERK) antibody; anti-E-Selectin antibody; anti-FAK antibody; anti-Fibronectin antibody; FITC-Goat Anti Mouse IgM antibody; anti-FOXP3 antibody; anti-GB 3 antibody; anti-GFAP (Glial Fibrillary Acidic Protein) antibody; anti-Giantin antibody; anti-GM130 antibody; anti-Goat a h Met antibody; anti-Golgin 97 antibody; anti-GRB2 antibody; anti-GRP78BiP antibody; anti-GSK-3Beta antibody; anti-Hepatocyte antibody; anti-HER-2 antibody; anti-HER-3 antibody; anti-Histone 3 antibody; anti-Histone 4 antibody; anti-Histone H2A X antibody; anti-Histone H2B antibody; anti-HSP70 antibody; anti-ICAM-1 antibody; anti-IGF-1 antibody; anti-IGF-1 Receptor antibody; anti-IGF-1 Receptor Beta antibody; anti-IGF-II antibody; anti-IKB-Alpha antibody; anti-IL6 antibody; anti-IL8 antibody; anti-Integrin beta 3 antibody; anti-Integrin beta 5 antibody; anti-Integrin b8 antibody; anti-Jagged 1 antibody; anti-protein kinase C Beta2 antibody; anti-LAMP-1 antibody; anti-M6P (Mannose 6-Phosphate Receptor) antibody; anti-MAPKAPK-2 antibody; anti-MEK 1 antibody; anti-MEK 2 antibody; anti-Mitochondrial Antigen antibody; anti-Mitochondrial Marker antibody; anti-Mitotracker Green FM antibody; anti-MMP-2 antibody; anti-MMP9 antibody; anti-Na+/K ATPase antibody; anti-Na+/K ATPase Alpha 1 antibody; anti-Na$^+$/K ATPase Alpha 3 antibody; anti-N-Cadherin antibody; anti-Nephrin antibody; anti-NF-KB p50 antibody; anti-NF-KB P65 antibody; anti-Notch 1 antibody; anti-OxPhos Complex IV—Alexa488 Conjugate antibody; anti-p130Cas antibody; anti-P38 MAPK antibody; anti-p44/42 MAPK antibody; anti-P504S Clone 13H4 antibody; anti-P53 antibody; anti-P70 S6K antibody; anti-P70 phospho kinase blocking peptide antibody; anti-Pan Cadherin antibody; anti-Paxillin antibody; anti-P-Cadherin antibody; anti-PDI antibody; anti-Phospho AKT antibody; anti-Phospho CREB antibody; anti-Phospho GSK-3-beta antibody; anti-Phospho GSK-3 Beta antibody; anti-Phospho H3 antibody; anti-Phospho MAPKAPK-2 antibody; anti-Phospho MEK antibody; anti-Phospho p44/42 MAPK antibody; anti-Phospho p53 antibody; anti-Phospho-NF-KB p65 antibody; anti-Phospho-p70 S6 Kinase antibody; anti-Phospho PKC (Pan) antibody; anti-Phospho S6 Ribosomal Protein antibody; anti-Phospho Src antibody; anti-Phospho-Bad antibody; anti-Phospho-HSP27 antibody; anti-Phospho-IKB-a antibody; anti-Phospho-p44/42 MAPK antibody; anti-Phospho-p70 S6 Kinase antibody; anti-Phospho-Rb (Ser807/811) (Retinoblastoma) antibody; anti-Phsopho HSP-7 antibody; anti-Phsopho-p38 antibody; anti-Pim-1 antibody; anti-Pim-2 antibody; anti-PKC β antibody; anti-PKC β11 antibody; anti-Podocalyxin antibody; anti-PR antibody; anti-PTEN antibody; anti-R1 antibody; anti-Rb 4H1 (Retinoblastoma) antibody; anti-R-Cadherin antibody; anti-RRM1 antibody; anti-S6 Ribosomal Protein antibody; anti-S-100 antibody; anti-Synaptopodin antibody; anti-Synaptopodin antibody; anti-Syndecan 4 antibody; anti-Talin antibody; anti-Tensin antibody; anti-Tuberlin antibody; anti-Urokinase antibody; anti-VCAM-1 antibody; anti-VEGF antibody; anti-Vimentin antibody; anti-ZAP-70 antibody; and anti-ZEB.

Fluorophores that may be conjugated to a primary antibody include but are not limited to Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, Fluor X, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br—Oregon, Lucifer Yellow, Alexa dye family, N-[6-(7-nitrobenz-2-oxa-1,3-diazol-4-yl)amino]caproyl] (NBD), BODIPY™, boron dipyrromethene difluoride, Oregon Green, MITOTRACKER™ Red, DiOC.sub.7 (3), DiIC.sub.18, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Lissamine, Umbelliferone, Tyrosine and Tryptophan. A wide variety of other fluorescent probes are available from and/or extensively described in the Handbook of Fluorescent Probes and Research Products 8.sup.th Ed. (2001), available from Molecular Probes, Eugene, Oreg., as well as many other manufacturers.

Further amplification of the signal can be achieved by using combinations of specific binding members, such as antibodies and anti-antibodies, where the anti-antibodies bind to a conserved region of the target antibody probe, particularly where the antibodies are from different species. Alternatively specific binding ligand-receptor pairs, such as biotin-streptavidin, may be used, where the primary antibody is conjugated to one member of the pair and the other member is labeled with a detectable probe. Thus, one effectively builds a sandwich of binding members, where the first binding member binds to the cellular component and serves to provide for secondary binding, where the secondary binding member may or may not include a label, which may further provide for tertiary binding where the tertiary binding member will provide a label.

The secondary antibody, avidin, strepavidin or biotin are each independently labeled with a detectable moiety, which can be an enzyme directing a colorimetric reaction of a substrate having a substantially non-soluble color reaction product, a fluorescent dye (stain), a luminescent dye or a non-fluorescent dye. Examples concerning each of these options are listed below.

In principle, any enzyme that (i) can be conjugated to or bind indirectly to (e.g., via conjugated avidin, strepavidin, biotin, secondary antibody) a primary antibody, and (ii) uses a soluble substrate to provide an insoluble product (precipitate) could be used.

The enzyme employed can be, for example, alkaline phosphatase, horseradish peroxidase, beta-galactosidase and/or glucose oxidase; and the substrate can respectively be an alkaline phosphatase, horseradish peroxidase, beta.-galactosidase or glucose oxidase substrate.

Alkaline phosphatase (AP) substrates include, but are not limited to, AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color).

Horseradish Peroxidase (HRP, sometimes abbreviated PO) substrates include, but are not limited to, 2,2' Azino-di-3-ethylbenz-thiazoline sulfonate (ABTS, green, water soluble), aminoethyl carbazole, 3-amino, 9-ethylcarbazole AEC (3A9EC, red). Alpha-naphthol pyronin (red), 4-chloro-1-naphthol (4C1N, blue, blue-black), 3,3'-diaminobenzidine tetrahydrochloride (DAB, brown), ortho-dianisidine (green), o-phenylene diamine (OPD, brown, water soluble), TACS Blue (blue), TACS Red (red), 3,3',5,5'Tetramethylbenzidine (TMB, green or green/blue), TRUE BLUE™ (blue), VECTOR™ VIP (purple), VECTOR™ SG (smoky blue-gray), and Zymed Blue HRP substrate (vivid blue).

Glucose oxidase (GO) substrates, include, but are not limited to, nitroblue tetrazolium (NBT, purple precipitate), tetranitroblue tetrazolium (TNBT, black precipitate), 2-(4-iodophenyl)-5-(4-nitorphenyl)-3-phenyltetrazolium chloride (INT, red or orange precipitate), Tetrazolium blue (blue), Nitrotetrazolium violet (violet), and 3-(4,5-dimethylthiazol-2-yl)-2,5-diphenyltetrazolium bromide (MTT, purple). All tetrazolium substrates require glucose as a co-substrate. The glucose gets oxidized and the tetrazolium salt gets reduced and forms an insoluble formazan that forms the color precipitate.

Beta-galactosidase substrates, include, but are not limited to, 5-bromo-4-chloro-3-indoyl beta-D-galactopyranoside (X-gal, blue precipitate). The precipitates associated with each of the substrates listed have unique detectable spectral signatures (components).

The enzyme can also be directed at catalyzing a luminescence reaction of a substrate, such as, but not limited to, luciferase and aequorin, having a substantially non-soluble reaction product capable of luminescencing or of directing a second reaction of a second substrate, such as but not limited to, luciferine and ATP or coelenterazine and $Ca.^{2+}$, having a luminescencing product.

The following references, which are incorporated herein in their entireties, provide additional examples: J. M Elias (1990) Immunohistopathology: A practical approach to diagnosis. ASCP Press (American Society of Clinical Pathologists), Chicago; J. F. McGinty, F. E. Bloom (1983) Double immunostaining reveals distinctions among opioidpeptidergic neurons in the medial basal hypothalamus. Brain Res. 278: 145-153; and T. Jowett (1997) Tissue In situ Hybridization: Methods in Animal Development. John Wiley & Sons, Inc., New York; J Histochem Cytochem 1997 December 45(12):1629-1641.

Cellular preparations may be subjected to in-situ hybridization (ISH). In general, a nucleic acid sequence probe is synthesized and labeled with either a fluorescent probe or one member of a ligand:receptor pair, such as biotin/avidin, labeled with a detectable moiety. Exemplary probes and moieties are described in the preceding section. The sequence probe is complementary to a target nucleotide sequence in the cell. Each cell or cellular compartment containing the target nucleotide sequence may bind the labeled probe. Probes used in the analysis may be either DNA or RNA oligonucleotides or polynucleotides and may contain not only naturally occurring nucleotides but their analogs such as dioxygenin dCTP, biotin dcTP 7-azaguanosine, azidothymidine, inosine, or uridine. Other useful probes include peptide probes and analogues thereof, branched gene DNA, peptidomimetics, peptide nucleic acids, and/or antibodies. Probes should have sufficient complementarity to the target nucleic acid sequence of interest so that stable and specific binding occurs between the target nucleic acid sequence and the probe. The degree of homology required for stable hybridization varies with the stringency of the hybridization. Conventional methodologies for ISH, hybridization and probe selection are described in Leitch, et al. In Situ Hybridization: a practical guide, Oxford BIOS Scientific Publishers, Microscopy Handbooks v. 27 (1994); and Sambrook, J., Fritsch, E. F., Maniatis, T., Molecular Cloning: A Laboratory Manual, Cold Spring Harbor Press (1989).

The present invention is further illustrated by the following examples, which should not be construed as limiting in any way. The contents of all cited references are hereby expressly incorporated by reference.

EXEMPLIFICATION

Example 1

Methodology—Using Publicly Available Tools

Figure 2:
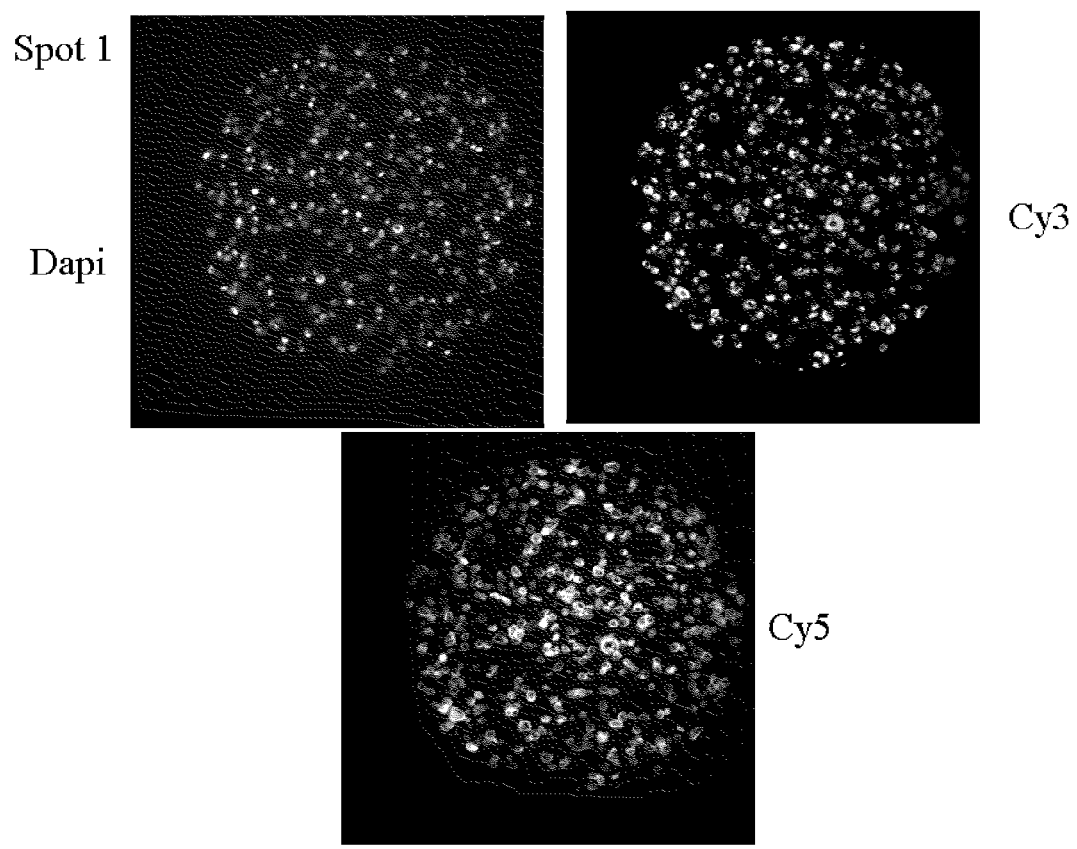
FIG. 2 shows a cell line stained with DAPI (nuclei), anti-Cytokeratin (Cy3), and anti-integrin alpha-V (Cy5).
Figure 3:
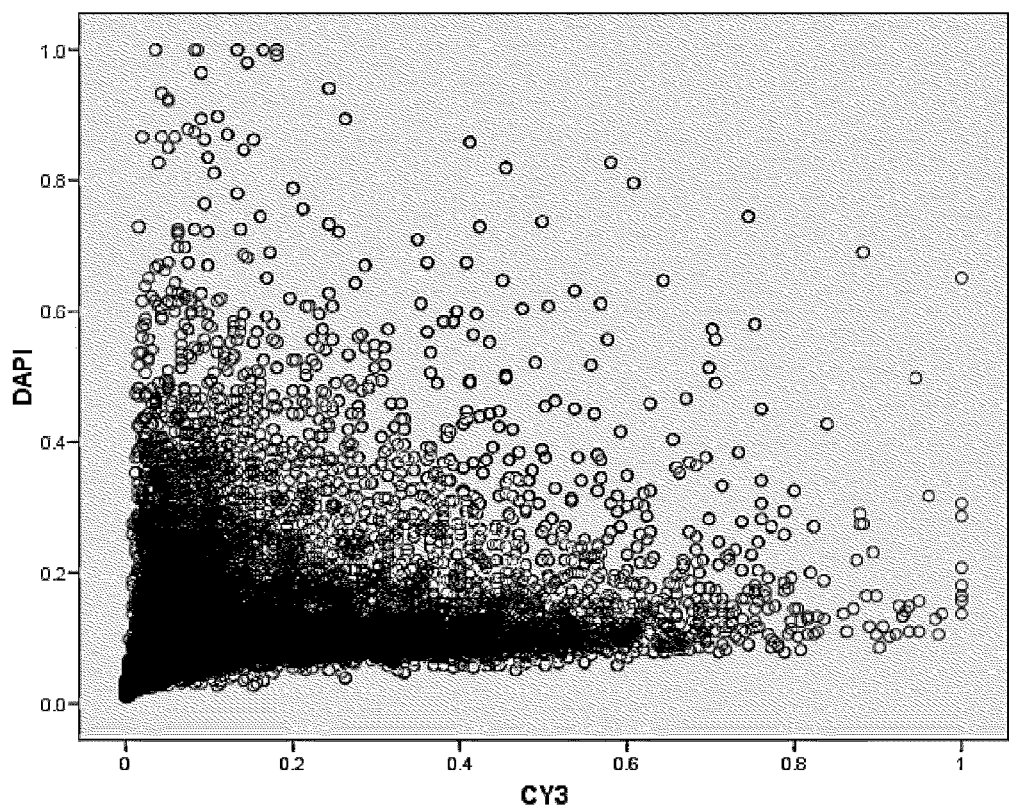
FIG. 3 is a scatter plot showing DAPI (norm) vs. Cy3 (norm).

To begin to address the feasibility of performing clustering algorithms on image data, SPSS (SPSS, Inc., Chicago, Ill.) statistical software package was applied in studies with data files representing pixel intensities for each pixel (DAPI, Cy3, and Cy5) from a selected high resolution image (e.g., 2048× 2048 pixels). FIG. 2 shows the images that were used in the first analysis, depicting a cell line control stained with DAPI (nuclei), anti-Cytokeratin (Cy3), and anti-integrin alpha-V (Cy5). For these images, every 64th pixel was outputted to the data file. FIG. 3 shows a scatter plot of normalized pixel intensities for DAPI and Cy3 (normalized on a 0-1 scale by dividing by max pixel intensity). Clustering normalized pixel values [using two-step cluster algorithm: log-likelihood distance; cluster limit=15] resulted in two clusters (Table 1).

TABLE 1

| Cluster Distribution | | | |
|---|---|---|---|
| | N | % of Combined | % of Total |
| Cluster 1 | 58719 | 89.6 | 89.6 |
| Cluster 2 | 6816 | 10.4 | 10.4 |
| Combined | 65535 | 100.0 | 100.0 |
| Total | 65535 | | 100.0 |

Figure 4:
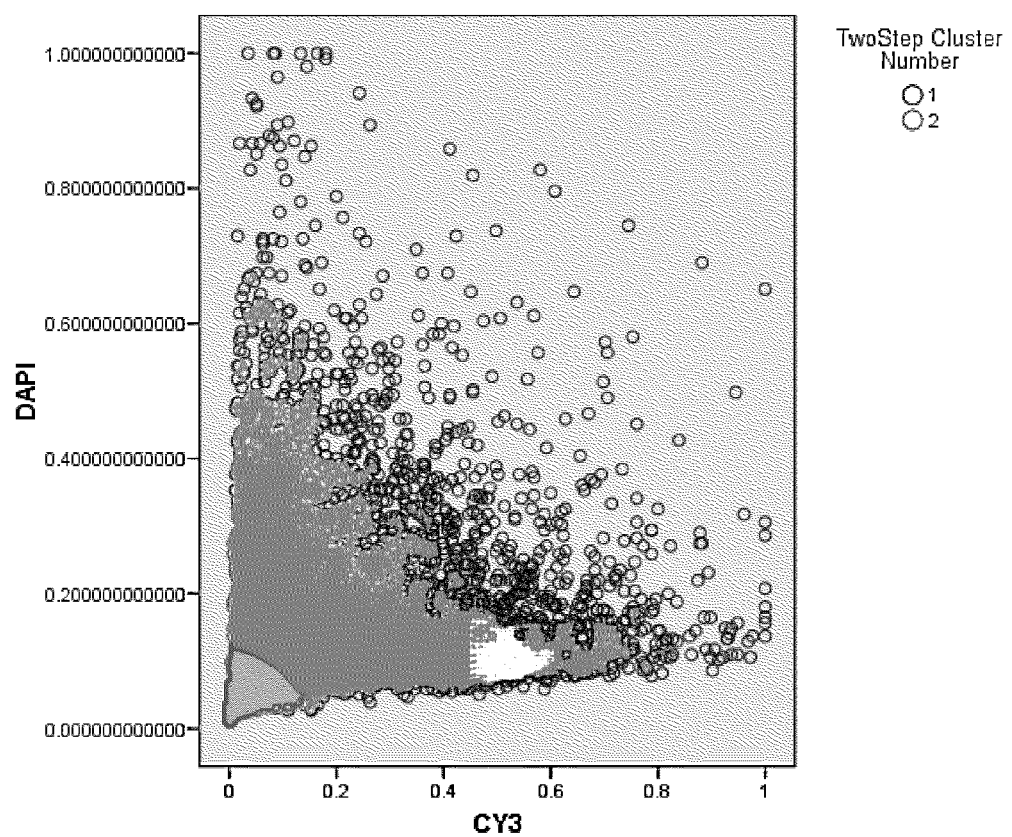
FIG. 4 presents data showing clustering using Log-Likelihood Distance (Auto).

Cluster 1 was the lowest value cluster and contained ~90% of the pixels for both Cy3 and DAPI. Visualization of the cluster assignments (FIG. 4) reveals Cluster 1 are pixels that represent low values in both DAPI and Cy3 with Cluster 2 representing pixels having value in both images. Cluster 1 thus defines pixels that fit criteria 1 from above. These are background pixels that have value in neither Cy3 nor DAPI. Therefore, this cluster can be removed from analysis.

To differentiate the subsequent three criteria, a metric termed, "Cy3 Percentage" was developed/defined whereby:

$$\frac{Cy3 \text{ Pixel Intensity (Normalized)}}{\left(\begin{array}{c} Cy3 \text{ Pixel Intensity } (NORM) + \\ DAPI \text{ Pixel Intensity } (NORM) \end{array}\right)}$$

Figure 5:
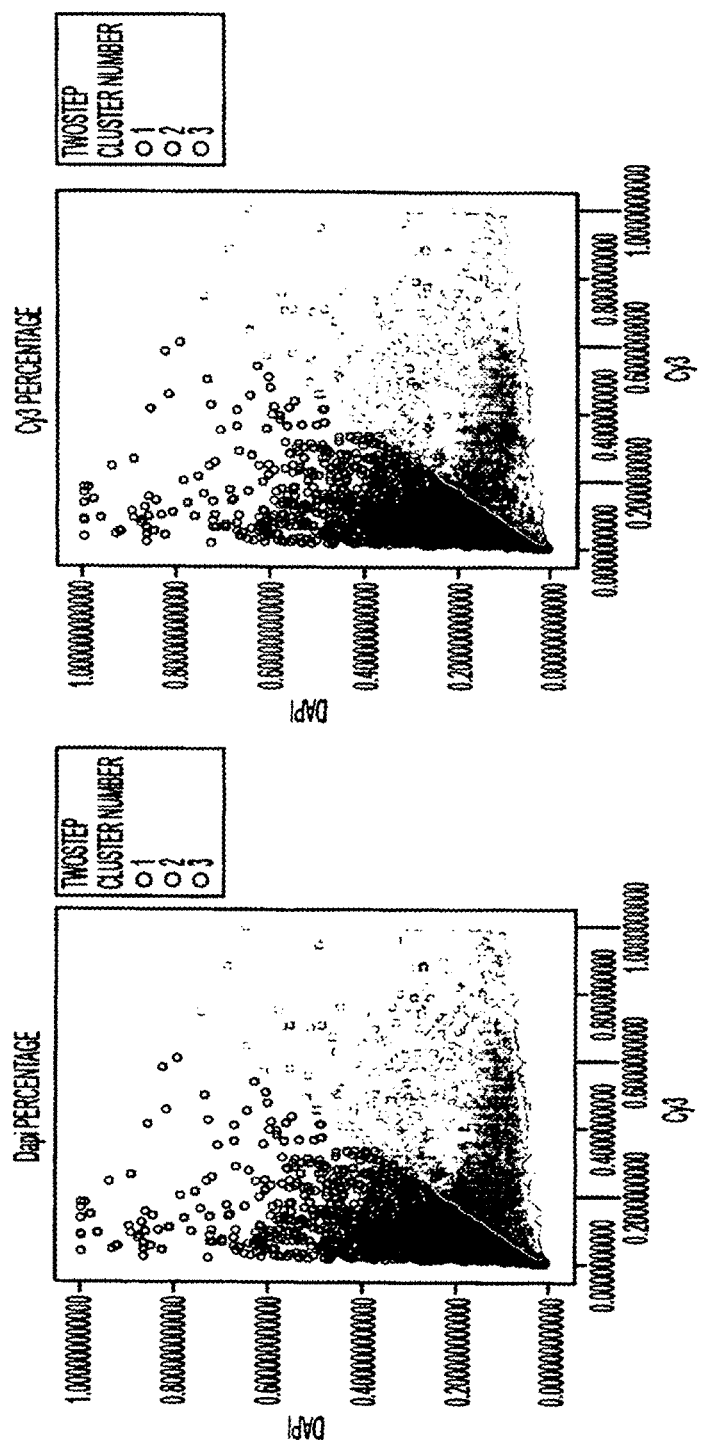
FIG. 5 presents data showing clustering of DAPI Percentage: Log Likelihood Distance (Force 3). Both produced equivalent clustering, use Cy3 percentage, taking the top cluster as Cy3-predominant positive pixels and the bottom cluster as DAPI-predominant positive pixels.

This yields a metric for the relative pixel intensity between Cy3 and DAPI. This could also be performed using DAPI as the numerator, wherein the approach yielded equivalent results (FIG. 5). Clustering on this method will indicate:

High DAPI intensity relative to Cy3 intensity: LOW Cy3 Percentage Cluster

High Cy3 intensity relative to DAPI intensity: HIGH Cy3 Percentage Cluster

High DAPI AND Cy3 intensity: MIDDLE Cy3 Percentage Cluster

Figure 6:
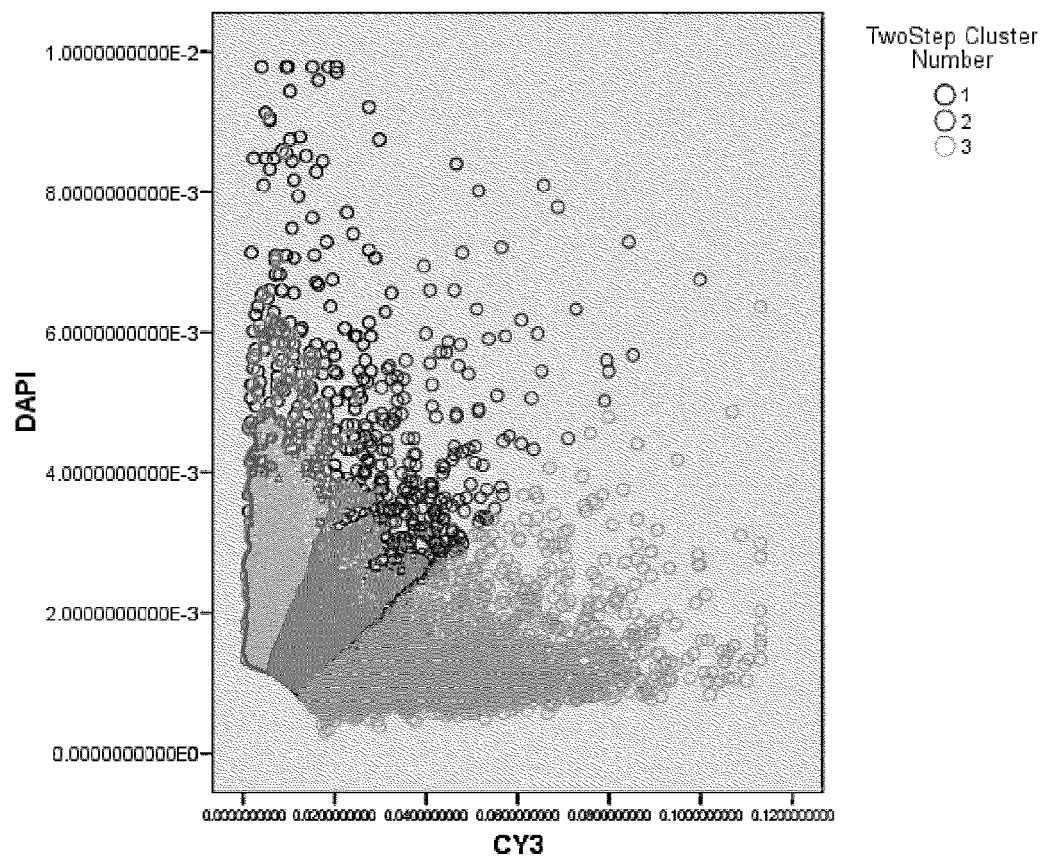
FIG. 6 shows "Signaling Cluster" Cy3 Percentage (based on normalized values) Log-Likelihood (Standardized)-Force 3.

Performing this clustering [using two-step cluster algorithm: log-likelihood distance; cluster limit=3], 3 clusters (Table 2 and FIG. 6) were observed representing, based on axes relationships, the above three criteria.

TABLE 2

Cluster Distribution

|  | N | % of Combined | % of Total |
|---|---|---|---|
| Cluster 1 | 1689 | 25.1 | 25.1 |
| Cluster 2 | 1645 | 24.5 | 24.5 |
| Cluster 3 | 3388 | 50.4 | 50.4 |
| Combined | 6722 | 100.0 | 100.0 |
| Total | 6722 |  | 100.0 |

Treating the "DAPI Cluster" (Cluster 1) and "Cy3 Cluster" (Cluster 3) separately to calculate a target AQUA® score [sum Cy5 pixel intensities in each cluster, divide by the total number of pixels in the cluster, multiply by a constant, 100,000] yielded AQUA® scores that fit with the expected biology of the target in that Cy3 expression was observed as greater than DAPI expression (Integrin is predominantly associated with the membrane/cytoplasm) as shown in Table 3. As additional proof of concept, high DAPI signal in DAPI pixels versus Cy3 pixels (Table 4) and higher Cy3 signal in Cy3 pixels versus DAPI pixels (Table 5) were observed by these methods. Similar results were observed when Euclidean distance algorithms were used rather than log-likelihood (Tables 6-8).

TABLE 3

Resulting AQUA® Scores, Log Likelihood Clustering

|  | Cy3 Pixels | DAPI Pixels | Relevant Ratio |
|---|---|---|---|
| AltP | 3102 | 976 | 3.18 |
| Cy3%-LL | 3630 | 1983 | 1.83 |

**Summed Cy5 power in each cluster (DAPI cluster (bottom cluster); Cy3 cluster (top cluster)); divided by total number of pixels * 100000.

TABLE 4

Resulting AQUA® Scores, Log Likelihood Clustering

|  | Cy3 | DAPI | Relevant Ratio |
|---|---|---|---|
| AltP | NA | NA | NA |
| Cy3%-LL | 115 | 291 | 2.6 |

**Summed DAPI power in each cluster (DAPI cluster (bottom cluster); Cy3 cluster (top cluster)); divided by total number of pixels * 100000.

TABLE 5

Resulting AQUA® Scores, Log Likelihood Clustering

|  | Cy3 | DAPI | Relevant Ratio |
|---|---|---|---|
| AltP | NA | NA | NA |
| Cy3%-LL | 4014 | 767 | 5.28 |

**Summed Cy3 power in each cluster (DAPI cluster (bottom cluster); Cy3 cluster (top cluster)); divided by total number of pixels * 100000

TABLE 6

Resulting AQUA® Scores, Euclidean Distance Clustering

|  | Cy3 Pixels | DAPI Pixels | Relevant Ratio |
|---|---|---|---|
| AltP | 3102 | 976 | 3.18 |
| Cy3%-LL | 3560 | 2396 | 1.49 |

**Summed Cy5 power in each cluster (DAPI cluster (bottom cluster); Cy3 cluster (top cluster)); divided by total number of pixels * 100000.

TABLE 7

Resulting AQUA® Scores, Euclidean Distance Clustering

|  | Cy3 | DAPI | Relevant Ratio |
|---|---|---|---|
| AltP | NA | NA | NA |
| Cy3%-LL | 321 | 535 | 1.6 |

**Summed DAPI power in each cluster (DAPI cluster (bottom cluster); Cy3 cluster (top cluster)); divided by total number of pixels * 100000

TABLE 8

Resulting AQUA® Scores, Euclidean Distance Clustering

|  | Cy3 | DAPI | Relevant Ratio |
|---|---|---|---|
| AltP | NA | NA | NA |
| Cy3%-LL | 7551 | 1163 | 6.5 |

**Summed Cy3 power in each cluster (DAPI cluster (bottom cluster); Cy3 cluster (top cluster)); divided by total number of pixels * 100000.

Example 2

Figure 7:
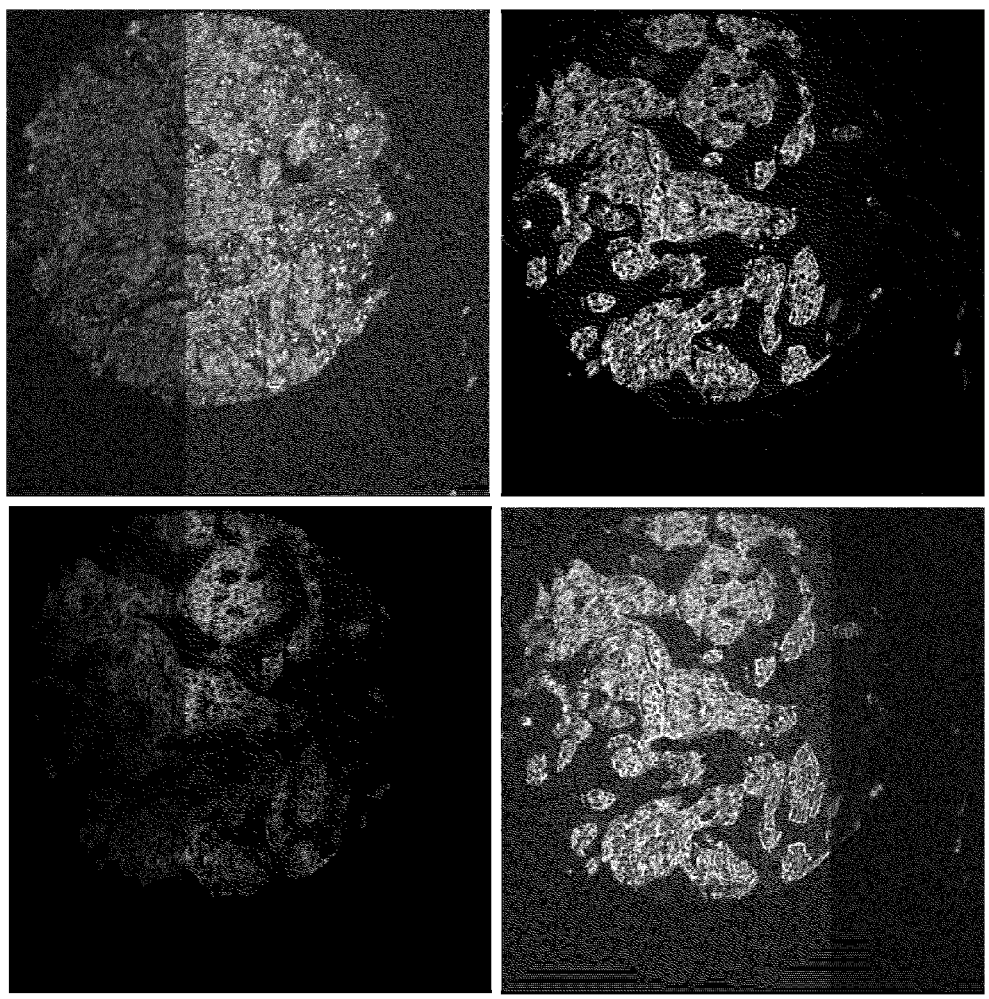
FIG. 7 shows staining of cell type Her2 Spot 17.

Data for every pixel image was obtained and analyzed for the images presented in FIG. 7 (Her2 stained breast cancer epithelium). First pass clustering was performed as before to remove background pixels (Table 9) followed by clustering the Cy3 percentage metric (Table 10).

TABLE 9

Cluster Distribution

|  | N | % of Combined | % of Total |
|---|---|---|---|
| Cluster 1 | 3145854 | 75.0 | 75.0 |
| Cluster 2 | 1048450 | 25.0 | 25.0 |
| Combined | 4194304 | 100.0 | 100.0 |
| Total | 4193404 |  | 100.0 |

TABLE 10

Cluster Distribution

|  | N | % of Combined | % of Total |
|---|---|---|---|
| Cluster 1 | 236673 | 22.6 | 22.6 |
| Cluster 2 | 296558 | 28.3 | 28.3 |
| Cluster 3 | 515219 | 49.1 | 49.1 |
| Combined | 1048450 | 100.0 | 100.0 |
| Total | 1048450 |  | 100.0 |

The resultant AQUA scores fit expectation in that increased Her2 expression in Cy3 relative to DAPI, increased DAPI in DAPI relative to Cy3, and increased Cy3 in Cy3 relative to DAPI (Tables 11-13). Furthermore, the clustering method exceeded the performance of the current AQUA® method as a high Cy3/DAPI ratio for Her2 was observed (see FIG. 7). Her2 is a predominantly cytoplasmic/membraneous protein.

TABLE 11

Resulting Cy5 AQUA ® Scores

|  | Cy3 Pixels | DAPI Pixels | Relevant Ratio |
|---|---|---|---|
| AltP | 617 | 346 | 1.78 |
| Pixel # | 304138 | 292536 |  |
| Cy3%-LL | 1133 | 290 | 3.9 |
|  | 515219 | 236673 |  |

**Summed Cy5 power in each cluster (DAPI cluster (bottom cluster); Cy3 cluster (top cluster)); divided by total number of pixels * 100000.

TABLE 12

Resulting DAPI AQUA ® Scores

|  | Cy3 | DAPI | Relevant Ratio |
|---|---|---|---|
| AltP | NA | NA | NA |
| Cy3%-LL | 309 | 547 | 1.8 |

**Summed DAPI power in each cluster (DAPI cluster (bottom cluster); Cy3 cluster (top cluster)); divided by total number of pixels * 100000

TABLE 13

Resulting Cy3 AQUA ® Scores

|  | Cy3 | DAPI | Relevant Ratio |
|---|---|---|---|
| AltP | NA | NA | NA |
| Cy3%-LL | 7551 | 1163 | 6.5 |

**Summed Cy3 power in each cluster (DAPI cluster (bottom cluster); Cy3 cluster (top cluster)); divided by total number of pixels * 100000.

Example 3

Figure 8:
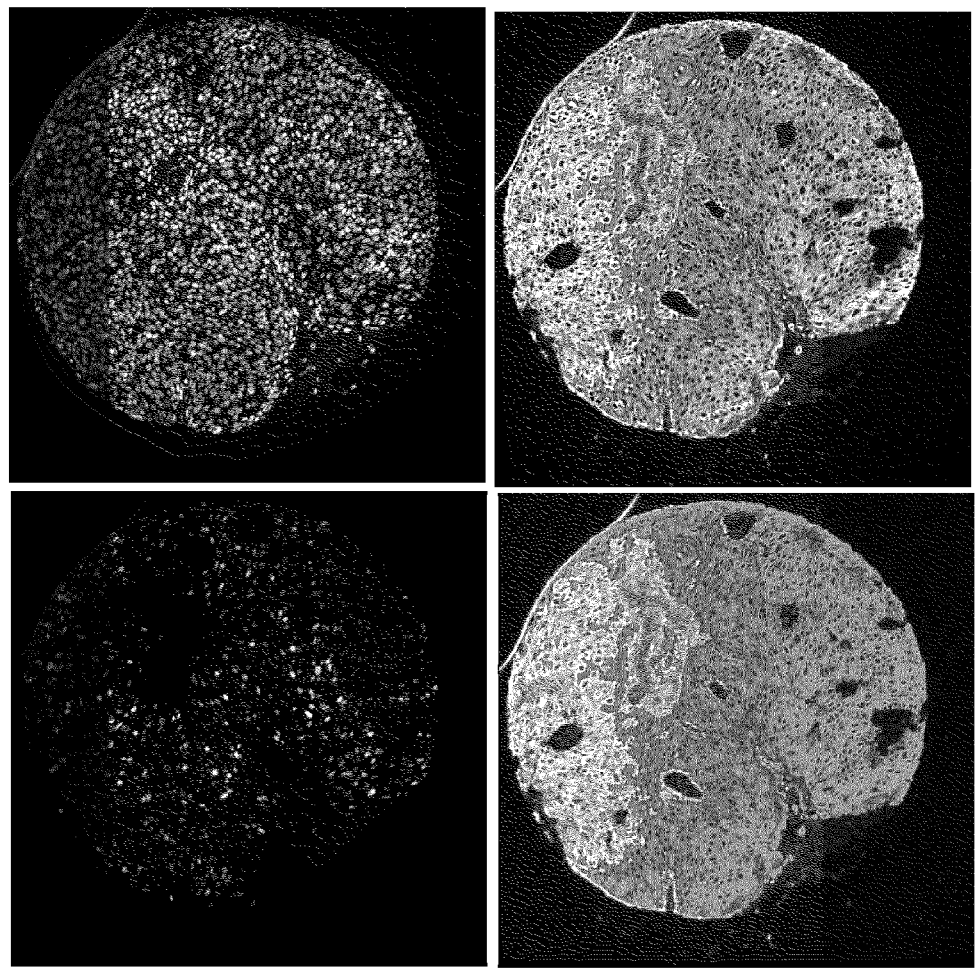
FIG. 8 shows staining of cell type p53 Spot 2.

Data for every pixel image was obtained and analyzed for the images presented in FIG. 8 (p53 stained cervical cancer epithelium). First pass clustering was performed as before to remove background pixels followed by clustering the Cy3 percentage metric (Table 14).

TABLE 14

Cluster Distribution

|  | N | % of Combined | % of Total |
|---|---|---|---|
| Cluster 1 | 1926335 | 45.9 | 45.9 |
| Cluster 2 | 776690 | 18.5 | 18.5 |
| Cluster 3 | 1491279 | 35.6 | 35.6 |
| Combined | 4194304 | 100.0 | 100.0 |
| Total | 4194304 |  | 100.0 |

Note first pass clustering resulted in 3 clusters. However, the background cluster (Cluster 1) is equivalent to the background cluster obtained when two clusters were "forced" (Table 15).

TABLE 15

Cluster Distribution

|  | N | % of Combined | % of Total |
|---|---|---|---|
| Cluster 1 | 1932895 | 46.1 | 46.1 |
| Cluster 2 | 2261409 | 53.9 | 53.9 |
| Combined | 4194304 | 100.0 | 100.0 |
| Total | 4194304 |  | 100.0 |

The resultant AQUA® scores fit expectation in that increased p53 expression in DAPI relative to Cy3, increased DAPI in DAPI relative to Cy3, and increased Cy3 in Cy3 relative to DAPI (Tables 16-18).

TABLE 16

Resulting Cy5 AQUA ® Scores

|  | Cy3 Pixels | DAPI Pixels | Relevant Ratio |
|---|---|---|---|
| AltP | 92 | 440 | 4.7 |
| Pixel Count: | 985051 | 455948 |  |
| Cy3%-LL | 190 | 735 | 3.9 |
| Pixels | 1484438 | 277449 |  |

**Summed Cy5 power in each cluster (DAPI cluster (bottom cluster); Cy3 cluster (top cluster)); divided by total number of pixels * 100000.

TABLE 17

Resulting Cy3 AQUA ® Scores

|  | Cy3 | DAPI | Relevant Ratio |
|---|---|---|---|
| AltP | NA | NA | NA |
| Cy3%-LL | 1753 | 477 | 3.7 |

**Summed DAPI power in each cluster (DAPI cluster (bottom cluster); Cy3 cluster (top cluster)); divided by total number of pixels * 100000.

TABLE 18

Resulting DAPI AQUA ® Scores

|  | Cy3 | DAPI | Relevant Ratio |
|---|---|---|---|
| AltP | NA | NA | NA |
| Cy3%-LL | 376 | 1793 | 4.8 |

TABLE 18-continued

Resulting DAPI AQUA ® Scores

| | Cy3 | DAPI | Relevant Ratio |
|---|---|---|---|

**Summed Cy3 power in each cluster (DAPI cluster (bottom cluster); Cy3 cluster (top cluster)); divided by total number of pixels * 100000.

Background pixels within the target image may also be an issue. In order to address this issue, clustering [using two-step cluster algorithm: log-likelihood distance; cluster limit=15] was performed on Cy5 pixel values to remove background (Table 19).

TABLE 19

Cluster Distribution

| | N | % of Combined | % of Total |
|---|---|---|---|
| Cluster 1 | 1879937 | 82.9 | 82.9 |
| Cluster 2 | 313604 | 13.8 | 13.8 |
| Cluster 3 | 74428 | 3.3 | 3.3 |
| Combined | 2267969 | 100.0 | 100.0 |
| Total | 2267969 | | 100.0 |

Dropping the bottom cluster as background improves area ratio metrics (Cytoplasm:Nucleus for Her2; and Nucleus:Cytoplasm for p53) as shown in Tables 20 and 21 (compare rows 2 and 3).

TABLE 20

P53: COMPARTMENT: Resulting Cy5 AQUA ® Scores

| | Cy3 Pixels | DAPI Pixels | Relevant Ratio |
|---|---|---|---|
| AltP | 53 | 440 | 4.7 |
| Pixel Count: | 985051 | 455948 | |
| Cy3%-LL-All | 190 | 735 | 3.9 |
| Target Pixels | 1484438 | 277449 | |
| Cy3%-LL-Top Target_Comp Pixels | 34 | 612 | 18 |
| Cy3%-LL-Top Target_Comp Pixels (only Target) | 797 | 1405 | 1.76 |

**Summed Cy5 power in each cluster (DAPI cluster (bottom cluster); Cy3 cluster (top cluster)); divided by total number of pixels * 100000.

TABLE 21

Her2: Resulting Cy5 AQUA ® Scores

| | Cy3 Pixels | DAPI Pixels | Relevant Ratio |
|---|---|---|---|
| AltP | 617 | 346 | 1.78 |
| Pixel# | 304138 | 292536 | |
| Cy3%-LL | 1133 | 290 | 3.9 |
| | 515219 | 236673 | |
| Cy3%-LL-Top Target_Comp Pixels | 612 | 145 | 4.2 |
| Cy3%-LL-Top Target_Comp Pixels (only Target) | 2379 | 2171 | 1.10 |

**Summed Cy5 power in each cluster (DAPI cluster (bottom cluster); Cy3 cluster (top cluster)); divided by total number of pixels * 100000.

Example 4

Construction of Tissue Microarrays and Immunohistochemical Staining Methods for Estrogen Receptor (ER) and HER2/neu and for Analysis of Nuclear Associated Beta-Catenin Tissue microarray design: Paraffin-embedded formalin-fixed specimens from 345 cases of node-positive invasive breast carcinoma were identified. Areas of invasive carcinoma, away from in situ lesions and normal epithelium, were identified and three 0.6 cm punch "biopsy" cores were taken from separate areas. Each core was arrayed into a separate recipient block, and five-micron thick sections were cut and processed as previously described (Konenen, J. et al., *Nat. Med.*, 4:844-7, 1987). Similarly, 310 cases of colon carcinoma were obtained and arrayed, as previously described (Chung, G. et al., *Clin. Cancer Res.* (In Press)). Immunohistochemistry: Pre-cut paraffin-coated tissue microarray slides were deparaffinized and antigen-retrieved by pressure-cooking (Katoh, A. K. et al., *Biotech. Histochem.*, F2:291-8, 1997). Slides were stained with antibodies to one of three target antigens: monoclonal anti-E.R. (mouse, Dako Corporation, Carpinteria, Calif.), polyclonal anti-HER2/neu (rabbit, Dako Corp.), monoclonal (mouse clone 14, BD Transduction Labs, San Diego, Calif.) anti-beta-catenin, or polyclonal rabbit anti-betacatenin. Primaries were incubated overnight at 4° C. A corresponding goat antimouse or anti-rabbit secondary antibody conjugated to a horseradish peroxidase decorated dextran-polymer backbone was then applied for 1 hr (Envision, DAKO Corp.). Target antigens were either visualized with a visible light chromagen (Diaminobenzidine, DAKO) for visual analysis, or a fluorescent chromagen (Cy-5-tyramide, NEN Life Science Products, Boston, Mass.). Slides designated for automated analysis were counterstained with DAPI for visualization of nuclei, and either polyclonal rabbit anticytokeratin (Zymed, So. San Francisco, Calif.) or rabbit anti-alpha-catenin to distinguish between tumor cells and stroma as well as to visualize the cell membrane. In many cases, exponentially subtracted images of histospots stained with anti-cytokeratin provided an acceptable marker for the cell membrane due to the sub-membranous coalescence of cytokeratin in tumor cells. These antibodies were visualized using either Cy3- or Alexa 488-conjugated goat anti-mouse or anti-rabbit secondary antibodies (Amersham, Piscataway, N.J. and Molecular Probes, Eugene, Oreg.). Slides designated for visual inspection were counterstained with ammonium hydroxide acidified hematoxylin. Manual examination of microarrays for E.R., HER2/neu, and beta-catenin levels has been previously described (Snead, D. R. et al., *Histopathology*, 23:233-8, 1993).

Example 5

Clustering AQUA® Analysis

The Automated QUantitative Analysis platform (AQUA® platform) is an automated fluorescence-based image analysis platform used for the objective and reproducible quantification of protein expression in specific cellular and sub-cellular compartments using the Pixel-based Locale Assignment for Compartmentalization of Expression (PLACE) algorithm Inherent to PLACE is a user-defined step whereby specific pixel intensity thresholds must be set manually to differentiate background from signal-specific pixels within multiple compartment images. To reduce operator time, remove operator-to-operator variability, and to obtain objective and optimal pixel separation for each image, a dichotomous, unsupervised pixel-based clustering algorithm (K-means clustering-based mathematics) allowing for the objective and automated differentiation of signal from background as well as differentiation of compartment-specific pixels (e.g., DAPI v. Cy3) on an image-by-image basis, is herein described. This new algorithm was tested by quantifying compartment-specific estrogen receptor (ER), progesterone receptor (PR), Her2 expression on large cohort (n=682) of breast cancer patients with a high degree of correlation (R=0.992, 0.987 and 0.990 respectively) with conventional AQUA® analysis using manual threshold settings as determined by an experienced operator. Expression scores obtained by clustering AQUA (c-AQUA) maintained equivalent quantitative relationships as shown by comparable data clustering and associated survival outcomes. Although either system is suitable for the methods of the invention, this new clustering algorithm enhances the efficiency and objectivity of the current AQUA® platform.

Methods

Cohort: A large breast cancer cohort in tissue microarray (TMA) format was employed in these studies to test C-AQUA algorithms. This cohort from the Yale Tissue Microarray Facility (YTMA49) has been described in detail previously (Dolled-Filhart, M. et al., *Clin. Cancer Res.*, 12:6459-68, 2006). Briefly, the breast cohort (n=652) of invasive ductal carcinoma serially collected from the Yale University Department of Pathology from 1961 to 1983. Also on the array are a selection of normal tissue and cell line controls. The mean follow-up time is 12.8 years with a mean age of diagnosis of 58.1 years. This cohort contains approximately half node-positive and half node-negative specimens.

Immunofluoresence staining. YTMA49 was staining using an indirect immunofluorescence protocoll. In brief, pre-cut paraffin-coated tissue microarray slides were de-paraffinized and antigen-retrieved by heat-induced epitope retrieval in 10 mM Tris (pH 9.0). Using an auto-stainer (LabVision, Fremont, Calif.), slides were pre-incubated with Background Sniper (BioCare Medical, Concord, Calif.). Slides were then incubated with primary antibodies against ER (Dako, Carpinteria, Calif.), clone 1D5, 1:200 dilution), PR (Dako (Carpinteria, Calif.), mouse monoclonal clone PgR636, 1:1000 dilution), or Her2 (Dako (Carpinteria, Calif.), rabbit polyclonal, 1:8000 dilution) and pan-cytokeratin (rabbit polyclonal, 1:200 dilution, DAKO, Carpinteria, Calif.) diluted in DaVinci Green (BioCare Medical, Concord, Calif.) for 1 hour at RT. Slides were washed 3×5 min with 1×TBS containing 0.05% Tween-20. Corresponding secondary antibodies were diluted in Da Vinci Green and incubated for 30 minutes at room temperature. These included either antibodies directly conjugated to a fluorophore for anti-cytokeratin (Alexa 555-conjugated goat anti-rabbit; 1:100, Molecular Probes, Eugene, Oreg.), and/or conjugated to a horseradish peroxidase (HRP) for ER, PR, and Her2 (Dako, Carpinteria, Calif.), anti-mouse or -rabbit Envision (Dako, Carpinteria, Calif.)). Slides were again washed 3×5 min with TBS containing 0.05% Tween-20. Slides were incubated with a fluorescent chromagen (Cy-5-tyramide, NEN Life Science Products, Boston, Mass.), which, like DAB, is activated by HRP and results in the deposition of numerous covalently associated Cy-5 dyes immediately adjacent to the HRP-conjugated secondary antibody. Cy-5 (red) was used because its emission peak is well outside the green-orange spectrum of tissue auto-fluorescence. Slides for automated analysis were cover slipped with an anti-fade DAPI-containing mounting medium (ProLong Gold, Molecular Probes, Eugene, Oreg.).

Image Acquisition: Automated image capture was performed by the HistoRx PM-2000™, which has previously been described in detail (Camp, R. et al., *Nat. Med.*, 8:1323-1327, 2002; Giltnane, J. & Rimm, D., *Nat. Clin. Pract. Oncol.*, 1:104-11, 2004; Cregger, M. et al., *Arch. Pathol. Lab. Med.*, 130:1026-30, 2006). High-resolution, 8 bit (resulting in 256 discrete intensity values per pixel of an acquired image) digital images of the cytokeratin staining visualized with Cy3, DAPI, and target staining with Cy5 were captured and saved for every histospot on the array. Pixels were written to image files as a function of power (Power (P)=((Pixel Intensity/256)/exposure time) to help compensate for experimental variations in staining intensity. In and out-of-focus images were taken for each channel for future use with the traditional AQUA® script and validation program.

Traditional AQUA® analysis: AQUA® analysis was performed. In brief, a tumor-specific mask is generated by manually thresholding the image of a marker (cytokeratin) that differentiates tumor from surrounding stroma and/or leukocytes. This creates a binary mask (each pixel is either 'on' or 'off'). Thresholding levels were verified, and adjusted if necessary, by spot-checking a small sample of images and then remaining images are automatically masked using the single determined threshold value. All subsequent image manipulations involve only image information from the masked area. Next, two images (one in-focus, one out of focus, taken 6 μm deeper into the sample) are taken of the compartment-specific tags and the target marker. A percentage of the out-of-focus image is subtracted from the in-focus image, based on a pixel-by-pixel analysis of the two images using an algorithm called RESA (Rapid Exponential Subtraction Algorithm). The RESA algorithm enhances the interface between areas of higher intensity staining and adjacent areas of lower intensity staining, allowing easier assignment of pixels to background and adjacent compartments. Finally, the PLACE algorithm assigns each pixel in the image to a specific sub-cellular compartment. Pixels that cannot be accurately assigned to a compartment within a user-defined degree of confidence (100% in this case) are discarded. For example, pixels where the nuclear and cytoplasmic pixel intensities are too similar to be accurately assigned are negated (usually comprising <8% of the total pixels). Once each pixel is assigned to a sub-cellular compartment (or excluded as described above), the signal in each location is summed. These data are saved and can subsequently be expressed either as a percentage of total signal or as the average signal intensity per compartment area. Images were validated according to the following: 1)>2% tumor area covered, 2) Images in bottom 10% of DAPI and/or Cy3 total intensity removed, 3) DAPI AQUA® score ratio (DAPI measured in nucleus/DAPI measured in cytoplasm) >1.5.

Clustering AQUA® Algorithm (C-AQUA): Tumor masks were applied to the images to exclude any regions of non-tissue or non-tumor and consider only tumor tissue for analysis (as in the traditional experiment described above, however, a fixed set of parameters is used for all experiments). This also improves the sensitivity and computational efficiency of the method by removing a large number of non-contributing pixels (for example, in a high resolution image of a 0.6 mm histospot, taken at 20× objective power, <50% of the pixels will represent tissue). Generating the tumor mask is accomplished as described above and using values that have been defined by examination of a number of different samples.

Figure 9:
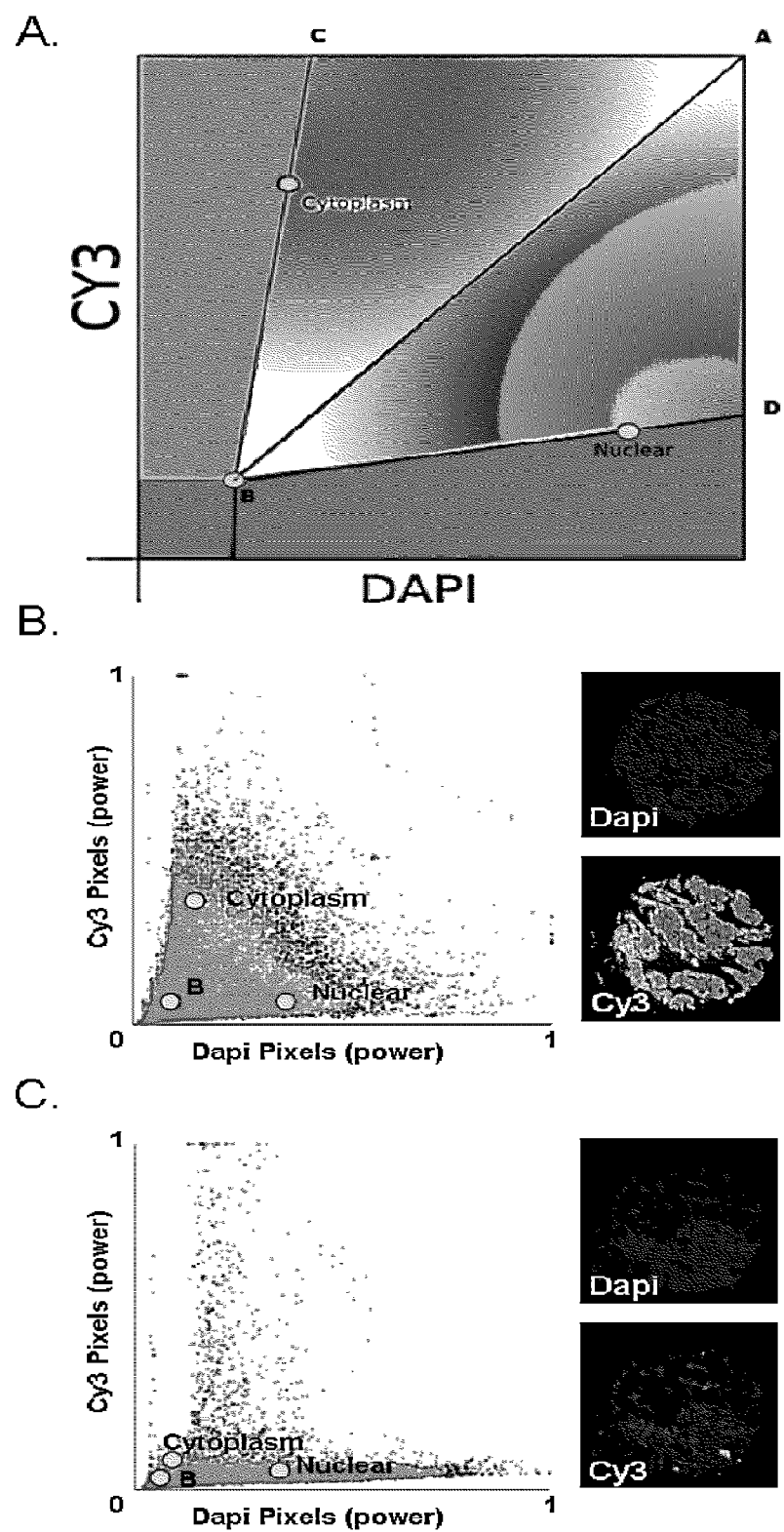
FIGS. 9A through 9C is are plots showing clustering analysis.

Image segmentation by clustering was accomplished using k-means clustering based on Euclidean distances (Jain, A. et al., *ACM Computing Surveys*, 31:264-323, 1999). First, all pixels were assigned characteristics based on power (see image acquisition) reported for compartment images, and can be represented as coordinates (PDAPI, Pcy3). As a result of this, pixels could be presented in a 2-D scatter-plot of compartment intensities (FIGS. 9A-C). The model used to perform the image segmentation asserts that pixels will fall into two classifications: 1) Those that have low signal in all compartments tested (i.e., background), and 2) Pixels with the property that one compartment marker shows higher staining than the others (e.g., higher Cy3 intensity than DAPI). For the data presented here, for two sub-cellular compartments, this would result in the need to identify three data centroids. The selection of initial value positions is important because it can impact how long the k-means algorithm will take to converge on a solution and prevent 'swapping' of centers, which would result in incorrect assignment. For the model described here, the background cluster is initialized to the origin while the cytokeratin and nuclear centers are initialized to their respective maximum values and zero (e.g., for the DAPI marker, the initial value is (PDAPI(max), 0). Pixels are then assigned to each cluster based on Euclidean distance. Cluster centroid values are then calculated and cluster pixel membership is re-assessed. The method runs iteratively and terminates after there is convergence (no membership changes) or 30 iterations.

Once cluster centroids have been defined, error checking occurs to detect conditions that may result in erroneous results. The first condition is if there is not enough signal in either one of the compartments, which will result in a segregation of the compartment based upon background noise. To detect this, a method is implemented that will compare each compartment center to the background cluster center. If a compartment center is within one standard of the foreground membership to the background cluster, the data point will be flagged and excluded from analysis. The second error check derives from the fact that the algorithm also detects the amount of area that is producing a viable signal. Should this area be too small to get a good sample size, the spot should be flagged and omitted from analysis since it is underrepresented. For the present system, which is equipped with a 2048×2048 CCD chip for acquiring images, the number of pixels reported must be greater than 210,000 pixels (5%). FIG. 9B shows an image that passes all quality control specifications whereas FIG. 9C shows an image that fails due to cluster distance failure in the Cy3 channel.

From examination of the scatter plots in FIGS. 9B and 9C, it can be seen that there will generally be pixels that have intensities higher than background, but have similar intensity contribution for each channel. Thus, once convergence is reached, a geometric method is then used to further define the certainty of a pixel as being a member of either cluster. Each pixel is characterized based upon its location in the cluster and proximity to other clusters. If both the Cy3 and DAPI pixels value are less than B, then there is zero certainty in both compartments and the pixel value is set to zero in both compartments (FIG. 9A). This represents background in the image. If Cy3 is greater than B and DAPI is less than B, then there is 100% probability for cytoplasm and 0% probability for nuclear (FIG. 9A). Conversely, if DAPI is greater than B and Cy3 is less than B, then there is 100% probability for nuclear and 0% probability for cytoplasm (FIG. 9A). For values in the center region of the scatter-plot that are not definitively assigned to either compartment, a probability function region is defined by the triangles ABC and ABD. In these regions, pixels are assigned to either Cy3 (triangle ABC) or DAPI (triangle ABD) exclusively. However, their contribution to the overall calculation is modified by their location within the triangles. Pixels in triangle ABC are assigned a probability based on their proximity to the vertices. Probabilities for pixels within the triangular regions are calculated via a well defined and continuous function that ranges from 0 to 1 (100% probability). As a pixel approaches C, the value approaches 100%, as a pixel approaches the vertices A or B (or the line segment connected A and B) the value approaches zero. Triangle ABD follows the same logic, with values approaching 100% as pixels approach the vertex D.

Results

Comparison of PLACE algorithms for compartment assignment: AQUA® analysis and C-AQUA analysis was performed on the same set of acquired and validated images (n=388 out of a total possible of 652). Although the results are similar, an operator was required to determine setup and threshold levels to generate images, whereas the associated images generated with C-AQUA were generated automatically, in an unsupervised fashion.

Figure 10:
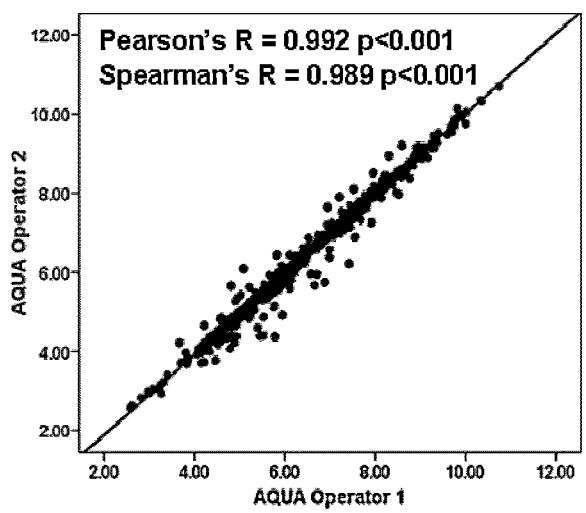
FIGS. 10A and 10B are plots showing comparisons between AQUA® and C-AQUA analysis.
Figure 10:
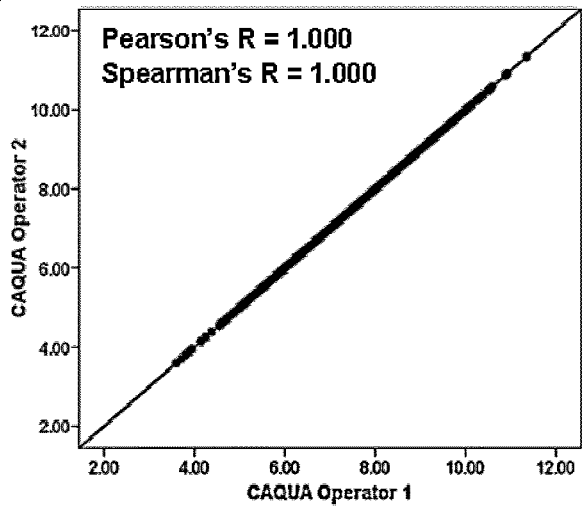

Two operators set up a traditional AQUA® and C-AQUA experiment on the same data set. Setup for a the traditional AQUA® experiment took an average of 20 minutes, whereas average set up time for C-AQUA was less than 2 minutes and did not require subjective operator intervention. Regression analysis between two operators for the two methods is shown in FIG. 10. Although highly correlative (FIG. 10A; Pearson R=0.992, p<0.001; Spearman's R=0.989, p<0.001), resultant AQUA® scores from AQUA® analysis was nonetheless different between operators, whereas AQUA® scores generated with C-AQUA were identical (FIG. 10B; Pearson R=1.000, p=0; Spearman's R=1.000, p=0).

Linear regression analysis was performed to examine overall comparisons for all images. Comparison of nuclear compartment size showed a highly significant correlation between conventional AQUA® analysis and C-AQUA (FIG. 10A; Pearson's R=0.779 (p<0.001); Spearman's R=0.793 (p<0.001)). Cytoplasmic compartment size was also significantly correlated (FIG. 10B; Pearson's R=0.923; Spearman's R=0.914 (p<0.001)). These data not only demonstrate the ability of C-AQUA to establish cellular compartments comparable to that of conventional AQUA®/PLACE algorithms, but also demonstrate that C-AQUA compartmentalization is not absolutely equivalent. This is due to the fact that compartmentalization is optimized for each image, rather than thresholding being universally applied across all images as with the conventional AQUA® analysis/PLACE algorithms.

Figure 11:
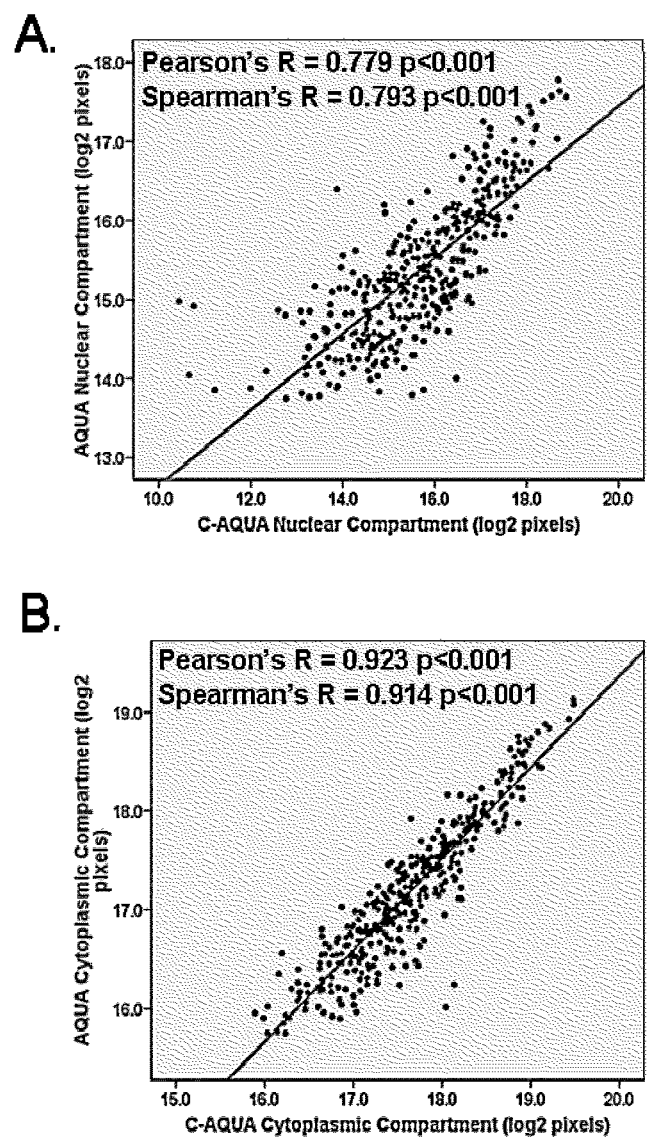
FIGS. 11A and 11B are plots showing comparisons between AQUA® and C-AQUA analysis.

Comparison of PLACE algorithms for expression score calculations: To confirm that C-AQUA produces equivalent AQUA® scores, conventional AQUA® analysis and C-AQUA analysis were performed for three common biomarkers of breast cancer; estrogen receptor (ER), progesterone receptor (PR), and Her2. Testing was performed on a large breast cancer cohort (n=607) of breast cancer patient samples in TMA format. AQUA® scores for both conventional AQUA® analysis and C-AQUA analysis in relevant cellular compartments produced highly correlative results in both value and rank-order analysis [FIG. 11A (ER, nucleus): Pearson's R=0.992 (p<0.001) and Spearman's R=0.993 (p<0.001); FIG. 11B (PR, nucleus): Pearson's R=0.987 (p<0.001) and Spearman's R=0.962 (p<0.001); FIG. 11C (Her2, cytoplasm/membrane): Pearson's R=0.990 (p<0.001) and Spearman's R=0.976 (p<0.001)].

Figure 12A:
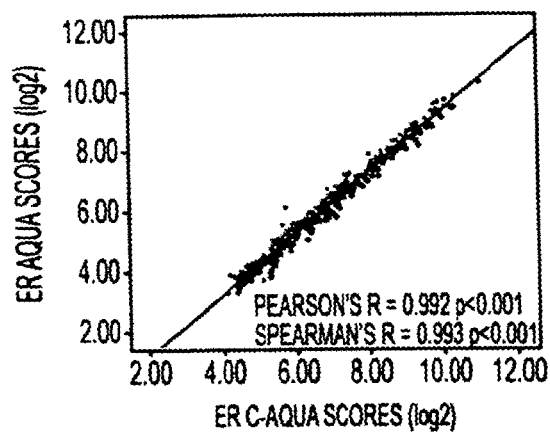
FIGS. 12A through 12C are plots showing comparisons between AQUA® and C-AQUA analysis.

Comparison of PLACE algorithms for survival outcomes: Although highly significant correlation between AQUA® scores obtained through conventional AQUA® analysis and C-AQUA was observed, it is important to demonstrate that equivalent data relationships are maintained such that comparable cut-points with respect to outcome (e.g., survival) can be obtained. To test this unsupervised log-likelihood distance clustering was performed for each set of AQUA® scores. For ER, two clusters were identified for both conventional AQUA® and C-AQUA scores with 95% overall agreement. ER expression in breast cancer is predictive of better survival. Kaplan-Meier survival analysis demonstrated AQUA® score clusters obtained for both traditional AQUA® analysis and C-AQUA analysis produced equivalent survival outcome results in that high ER expression significantly predicts an increase in five-year disease specific survival [FIG. 12A; traditional AQUA® analysis: 11.4% reduction in overall survival (log-rank p=0.018) from 80.9% (ER High) to 69.5% (ER Low); C-AQUA: 13.8% reduction in overall survival (log-rank p=0.005) from 81.6% (ER High) to 67.8% (ER Low)].

Figure 12B:
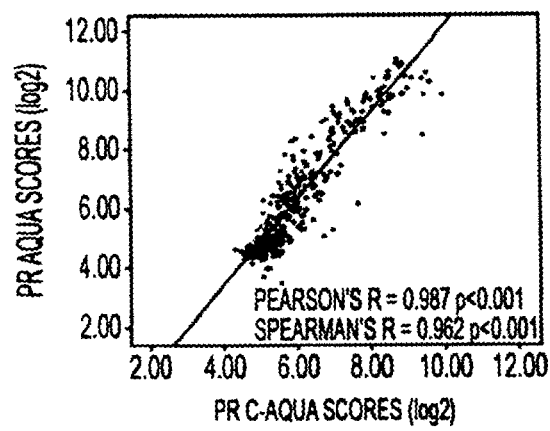

For PR, two clusters were identified for both conventional AQUA® analysis and C-AQUA scores with 83% overall agreement. PR expression in breast cancer is also predictive of better survival. Kaplan-Meier survival analysis demonstrated AQUA® score clusters obtained for both traditional AQUA® analysis and C-AQUA analysis produced equivalent survival outcome results in that high PR expression significantly predicts an increase in five-year disease specific survival [FIG. 12B; traditional AQUA®: 12.4% reduction in overall survival (log-rank p=0.021) from 84.2% (PR High) to 71.8% (PR Low); C-AQUA: 14.5% reduction in overall survival (log-rank p=0.001) from 83.3% (PR High) to 68.8% (PR Low)].

Figure 12C:
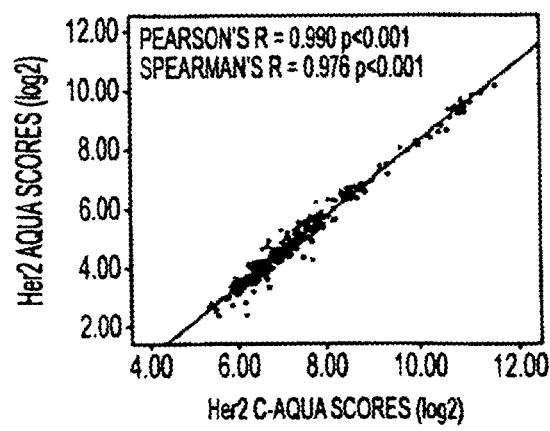

For Her2, three clusters were identified for both conventional AQUA® analysis and C-AQUA scores with 94% overall agreement. Her2 expression in breast cancer is predictive of decreased survival. Kaplan-Meier survival analysis demonstrated AQUA® score clusters obtained for both traditional AQUA® and C-AQUA analysis produced equivalent survival outcome results in that high Her2 expression significantly predicts decreased five-year disease specific survival [FIG. 12C; traditional AQUA®: 18.5% total reduction in overall survival (log-rank p=0.022) from 77.1% (Her2 Low) to 73.8% (Her2 Mid) to 58.6% (Her2 High); C-AQUA: 24.2% total reduction in overall survival (log-rank p=0.002) from 77.8% (Her2 Low) to 73.8% (Her2 Mid) to 53.6% (Her2 High)].

Discussion

The use of advanced image analysis is rapidly being adopted to facilitate analysis of samples in pathology laboratories. The associated automation, quantification and more objective analytical methods are providing pathologists access to improved and greater amounts of information. The AQUA® system is a robust and quantitative immunohistochemistry (IHC) platform is now a research system for biomarker characterization and discovery (Berger, A. et al., Cancer Res., 64:8767-8772, 2004; Camp, R. et al., Cancer Res., 63:1445-1448, 2003; Dolled-Filhart, M. et al., Clin. Cancer Res., 9:594-600, 2003; McCabe, A. et al., J. Natl. Cancer Inst., 97:1808-15, 2005). Unlike traditional IHC, the AQUA® system is objective and produces strictly quantitative in situ protein expression data on a continuous scale rather than subjective, categorical data. The AQUA® system takes advantage of the multiplexing power of fluorescence by using multiple markers to molecularly differentiate cellular and sub-cellular compartments within which simultaneous quantification of biomarkers-of-interest in specific cell types and sub-cellular compartments can be performed.

Clustering is a mathematical method whereby data is segregated based on the relationships of various properties inherent to each measurement (Miller, D. et al., Front. Biosci., 13:677-90, 2008), in this instance, the intensities of fluorescent measurements for pixels within an image. Clustering can be applied to multiple images of a single field of view using pixel intensities to ascribe centroids specific to background and signal or even different signaling levels. Application of these types of clustering algorithms to individual fluorescent images (e.g., DAPI or Cy3) allow for automated segmentation of background from specific signal for individual cellular compartments, just as user-defined thresholds accomplish.

A specific segmentation algorithm that results in clusters as described above is herein described, thus allowing for an automated PLACE-like algorithm that removes operator-to-operator variability and optimizes compartmentalization of expression on an image-by-image basis. C-AQUA shows a high degree of correlation with traditional AQUA® analysis as performed by an experienced operator.

Image segmentation such that protein expression can be quantified in specific cellular and sub-cellular compartments is an advance over other manual image quantification methods where these expression levels must be identified manually and the expression scored categorically by eye. It is also an advance over PLACE which does requires operator input, facilitated by image enhancement (RESA), to define specific pixel intensity thresholds to separate non-specific signal and background from specific signal in each compartment image.

Although other platforms exist for digitally performing pathological analysis, the quantitative AQUA® system provides advantages. The endpoint, however, in AQUA® analysis, which is image segmentation of not only specific signal from background but also two or more independent signals from independent images, presented a unique challenge. It was hypothesized that pixel intensities from two or more images could be clustered in parallel, thereby not only removing common background signal from all queried images but differentiating, with a high degree of confidence, specific signals from multiple images allowing for strict compartmentalization of expression for target-specific pixels. The beneficial characteristics of the PLACE algorithm's ability to segment images and compartmentalize expression is therefore maintained, but it is enhanced via in an automated method for compartmentalization and generating an AQUA® score.

Figure 13A:
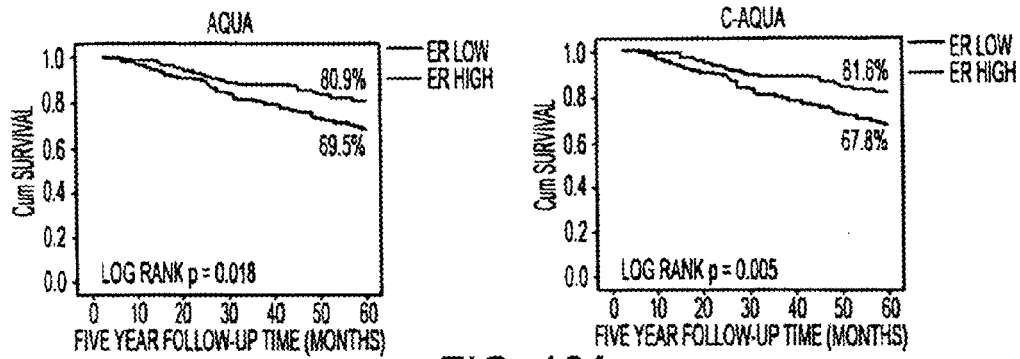
FIGS. 13A through 13C are plots showing comparisons between AQUA® and C-AQUA analysis. Survival outcome comparisons for FIG. 13A) ER, FIG. 13B) PR, and FIG. 13C) Her2 expression for AQUA® analysis (left) and C-AQUA analysis (right) showing similar survival outcomes based on cutpoint assignment as determined by unsupervised log-likelihood distance clustering [FIG. 13A) traditional AQUA®: 11.4% reduction in overall survival (log-rank p=0.018) from 80.9% (ER High) to 69.5% (ER Low); C-AQUA: 13.8% reduction in overall survival (log-rank p=0.005) from 81.6% (ER High) to 67.8% (ER Low)
Figure 13B:
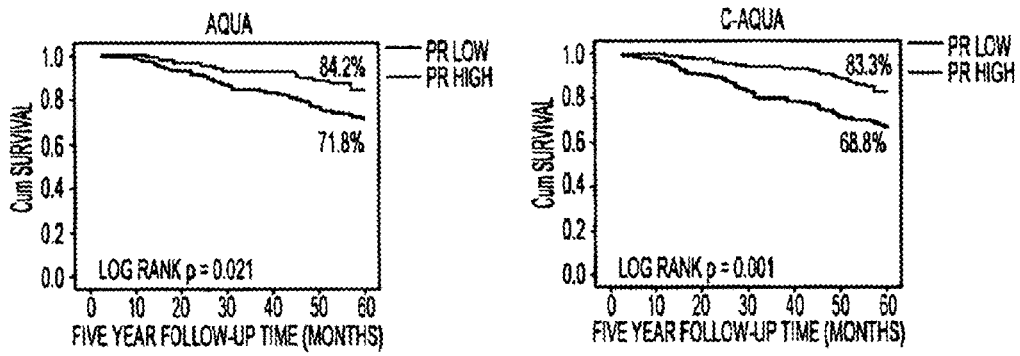
Figure 13C:
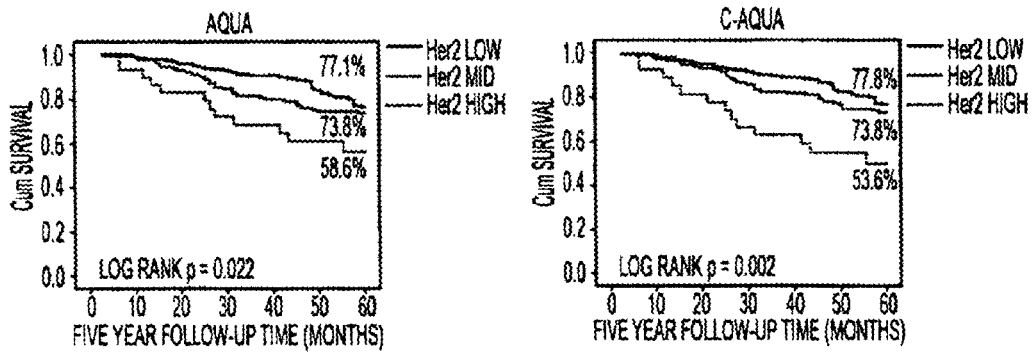

There are several key advantages to compartmentalization by the C-AQUA method. First, the operator input time is significantly reduced. With C-AQUA, the need to optimize thresholds is eliminated, thus reducing the setup time to 1-2 minutes. Second, an operator is not always capable of accurately analyzing an image using manual visual methods. Although trained operators typically determine approximately equivalent thresholds, changes in thresholds settings lead to differences in compartmentalization, which can potentially lead to difference in AQUA® scores (FIG. 10; comparisons are shown in FIG. 13). Given that accuracy and precision are of utmost importance, especially in a clinical setting, the enhancement of an already robust and reproducible system to a level of complete automation, and thus eliminating all sources of variability, is paramount. Third, user-defined thresholds must be equally applied across all images within a set being analyzed, whereas C-AQUA affords the opportunity to optimize compartmentalization on an image-by image basis.

It is possible to apply C-AQUA to more than two images allowing for the automated and optimal compartmentalization of three or more molecularly-defined compartments. For example, pixel assignment for nuclear (DAPI), cytoplasm (cytokeratin) and also membrane (pan-cadherin) could be achieved with the same level of accuracy and efficiency.

Example 6

Clustering AQUA® Analysis of PTEN Expression

A glioblastoma (GBM) TMA (110 GBM patients samples at 2× redundancy; median follow-up time: 13.2 months) was stained for detection of PTEN (Clone 138G6 mouse monoclonal, CST #9559) along with nuclear and non-nuclear compartments generally as described above, except S100 was used as the non-nuclear compartment marker. Images acquired as described above were analyzed using traditional AQUA® analysis and clustering AQUA® analysis.

Figure 14:
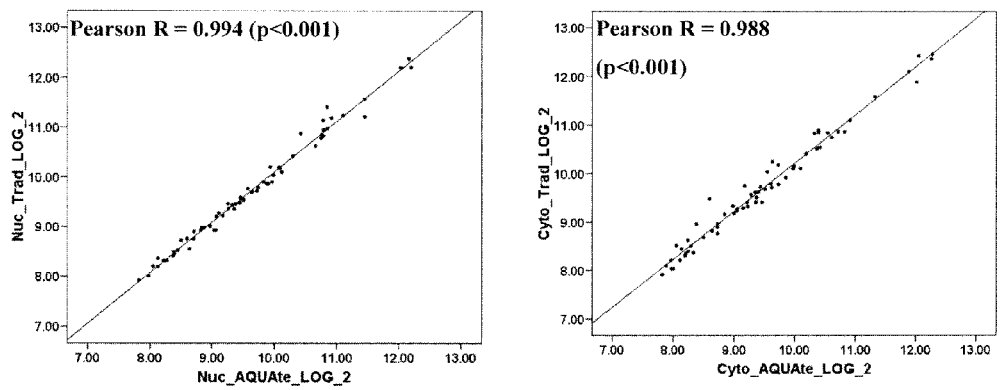
FIGS. 14A and 14B show PTEN expression AQUA® score comparison (linear regression) as determined by AQUA® and C-AQUA analysis.

PTEN AQUA® score comparison (linear regression) between AQUA® and C-AQUA analysis is shown in FIG. 14. FIG. 14A) Linear regression analysis for nuclear PTEN expression as determined by AQUA® analysis (Y-axis) and C-AQUA analysis (X-axis) with indicated Pearson's R. FIG. 14B) Linear regression analysis for cytoplasmic PTEN expression as determined by AQUA® analysis (Y-axis) and C-AQUA analysis (X-axis) with indicated Pearson's R values.

Figure 15:
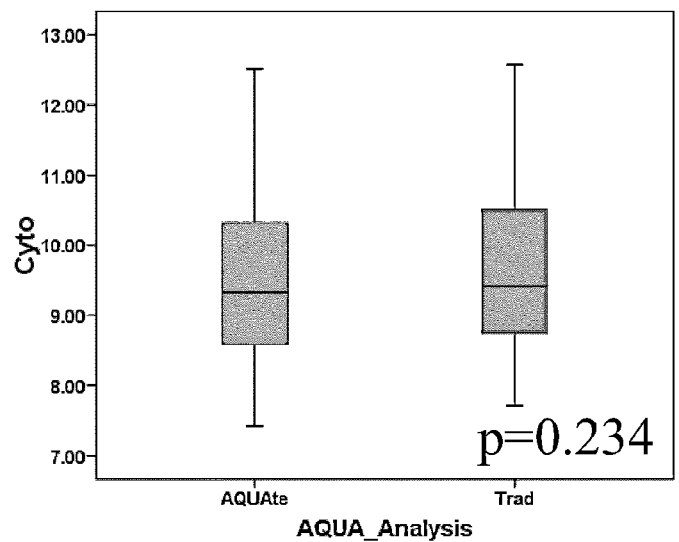
FIG. 15 PTEN cytoplasmic expression AQUA® scores.
Figure 16:
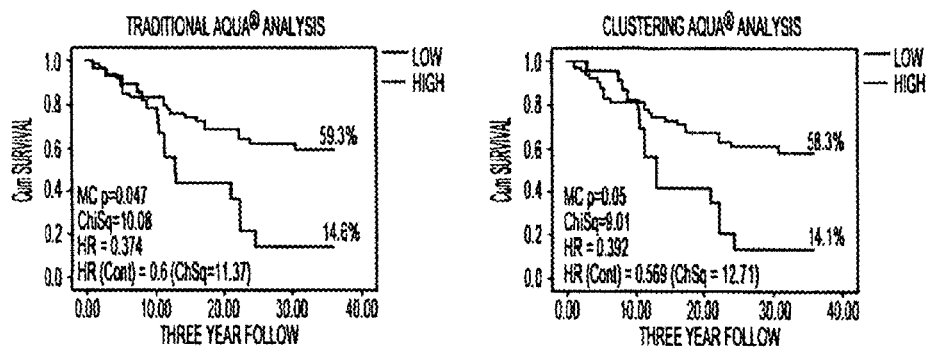
FIG. 16 shows the correlation of PTEN AQUA® scores derived by both methods to patient outcome is shown in Kaplan Meier curves. PTEN AQUA® scores were significantly correlated with patient survival. Low PTEN expression was associated with poor outcome compared to high PTEN expression.

PTEN cytoplasmic expression AQUA® scores are further described in FIG. 15. The correlation of PTEN AQUA® scores derived by both methods to patient outcome is shown in Kaplan Meier curves in FIG. 16. PTEN AQUA® scores were significantly correlated with patient survival. Low PTEN expression was associated with poor outcome compared to high PTEN expression.

Example 7

Clustering AQUA® Analysis of ERCC1 Expression

A lung cancer TMA [INSERT TMA DETAILS] was stained for detection of ERCC1 along with nuclear and non-nuclear compartments as described above. Images acquired as described above were analyzed using traditional AQUA® analysis and clustering AQUA® analysis.

Figure 17:
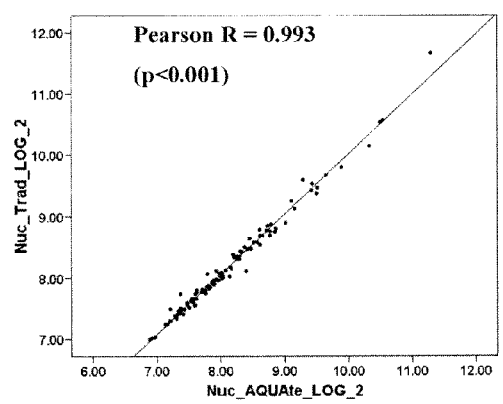
FIGS. 17A and 17B show ERCC1 expression AQUA® score comparison (linear regression) as determined by AQUA® and C-AQUA analysis.
Figure 17:
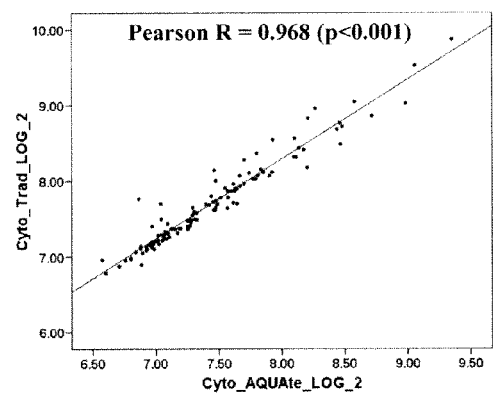

ERCC1 AQUA® score comparison (linear regression) between AQUA® and C-AQUA analysis is shown in FIG. 17. FIG. 17A) Linear regression analysis for nuclear ERCC1 expression as determined by AQUA® analysis (Y-axis) and C-AQUA analysis (X-axis) with indicated Pearson's R. FIG. 14B) Linear regression analysis for cytoplasmic ERCC1 expression as determined by AQUA® analysis (Y-axis) and C-AQUA analysis (X-axis) with indicated Pearson's R values.

Figure 18:
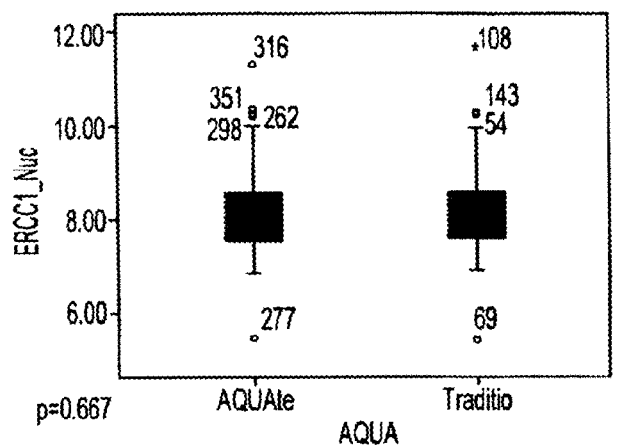
FIG. 18 ERCC1 cytoplasmic expression AQUA® scores.
Figure 19:
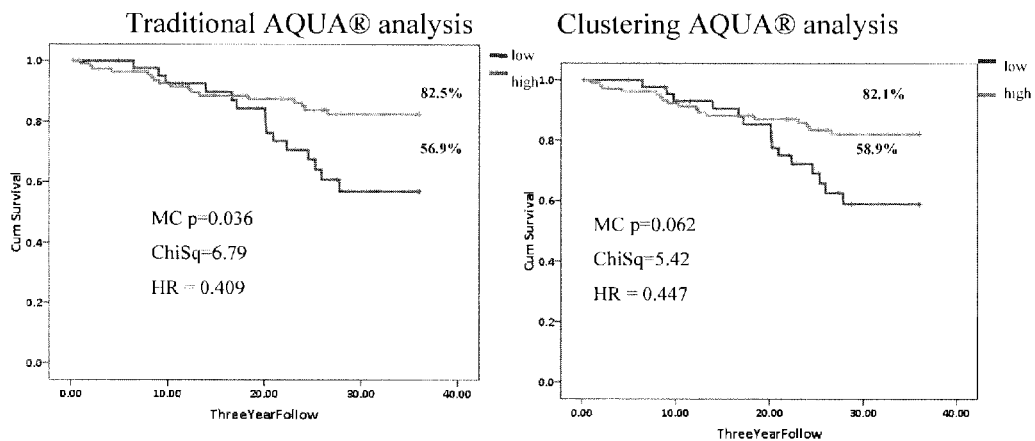
FIG. 19 shows the correlation of ERCC1 AQUA® scores derived by both methods to patient outcome is shown in Kaplan Meier curves. ERCC1 AQUA® scores were significantly correlated with patient survival. Low ERCC1 expression was associated with poor outcome compared to high ERCC1 expression.

ERCC1 cytoplasmic expression AQUA® scores are further described in FIG. 18. The correlation of ERCC1 AQUA® scores derived by both methods to patient outcome is shown in Kaplan Meier curves in FIG. 19. ERCC1 AQUA® scores were significantly correlated with patient survival. Low ERCC1 expression was associated with relatively poor outcome compared to high ERCC1 expression.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

What is claimed is:

1. A method for defining a first marker-defined biological compartment relative to a second marker-defined biological compartment present in a biological sample of interest, comprising comparing the intensity in each of the pixel locations in a first image of the first marker defined biological compartment with the intensity in each of the corresponding pixel locations of a second image of the second marker-defined biological compartment, wherein the first image was prepared using a first imaging agent that is specific for the first marker-defined biological compartment, and wherein the second image was prepared using a second imaging agent that is specific for the second marker-defined biological compartment, wherein differences in pixel intensity define the first marker-defined biological compartment relative to the second marker-defined biological compartment, assigning pixels to a cluster characterized by high first imaging agent intensity and low second imaging agent intensity to the first compartment;

assigning pixels to a cluster characterized by high second imaging agent intensity and low first imaging agent intensity to the second compartment; and assigning pixels to a cluster characterized by low first imaging agent intensity and low second imaging agent intensity to background and removing such pixels from further analysis, wherein any of the assigning steps are performed using a k means clustering method to determine a cluster membership for each pixel, and wherein the method is automated.

2. The method of claim 1, wherein the method is implemented by a computer.

3. The method of claim 1, wherein the pixels of the two images are plotted, wherein the axes of the plot comprise the intensity of the first imaging agent and the intensity of the second imaging agent.

4. The method of claim 1, further comprising assigning remaining pixels with first imaging agent intensity and second imaging agent intensity to either the first compartment or the second compartment based on probability.

5. The method of claim 1, further comprising assigning those remaining pixels with first imaging agent intensity and second imaging agent intensity to neither the first compartment nor the second compartment.

6. The method of claim 1, wherein the biological compartment is selected from the group consisting of: a cell type, sub-cellular compartment, a tissue compartment, and a localized cellular or tissue compartment.

7. The method of claim 6, wherein the biological compartment is a sub-cellular compartment selected from the group consisting of: cell nucleus, cytoplasm, nuclear membrane, cellular membrane, mitochondria, endoplasmic reticulum, peroxisome and lysosome.

8. The method of claim 6, wherein the biological compartment is a tissue compartment selected from the group consisting of: epithelium, stroma and mesothelia.

9. The method of claim 1, wherein the sample is a tissue sample, cell preparation or sub-cellular fraction.

10. The method of claim 1, further comprising defining a mask defined by the pixel intensity of the first and/or second imaging agent and defining compartment assignment for only those pixels within the mask.

11. The method of claim 1, further comprising incubating the sample with a first imaging agent that specifically labels the first marker-defined biological compartment, a second imaging agent that specifically labels a second marker-defined biological compartment.

12. A computer implemented method for defining a first marker-defined biological compartment relative to a second marker-defined biological compartment present in a biological sample comprising:
- a) incubating the sample with a first imaging agent that specifically labels the first marker-defined compartment, and a second imaging agent that specifically labels the second marker defined compartment;
- b) obtaining a first image of the first imaging agent labeled sample, and a second image of the second imaging agent labeled sample;
- c) determining a first and a second imaging agent intensity in each corresponding pixel location in the first and the second image;
- d) performing a clustering analysis on each pixel based on the first and the second imaging agent intensity of each pixel in each of the pixel to calculate clusters;
- e) assigning those pixels in the cluster characterized by high first imaging agent pixel intensity and low second imaging agent pixel intensity to the first compartment;
- f) assigning those pixels in the cluster characterized by high second imaging agent pixel intensity and low first imaging agent pixel intensity to the second compartment; and
- g) assigning those pixels in the cluster characterized by low first imaging agent pixel intensity and low second imaging agent pixel intensity to background and removing such pixels from further analysis, thereby defining a first marker-defined sub-cellular compartment relative to a second marker defined-sub-cellular compartment, wherein any of the assigning steps are performed using a k means clustering method to determine a cluster membership for each pixel, and wherein the method is automated.

13. A computer implemented method for defining a first marker defined sub-cellular compartment relative to a second marker defined sub-cellular compartment present in individual cells of interest contained in a tissue sample comprising:
- a) incubating the tissue sample with a first stain that specifically labels the first marker defined sub-cellular compartment, a second stain that specifically labels a second marker defined sub-cellular compartment,
- b) obtaining an image of each of the first and the second stain in the tissue sample using a microscope so as to obtain:
  - i) a first image of the first marker defined sub-cellular compartment;
  - ii) a second image of the second marker defined sub-cellular compartment; and
- c) determining the first and second stain intensity in each of the pixel locations in the first and the second image;
- d) plotting the pixels, where the axes of the plot comprise the intensity of the first stain and the intensity of the second stain;
- e) performing reiterative k-means clustering on the first and the second stain intensity in each of the pixel locations to calculate three clusters;
- f) assigning those pixels in the cluster characterized by high first stain intensity and low second stain intensity to the first compartment;
- g) assigning those pixels in the cluster characterized by high second stain intensity and low first stain intensity to the second compartment;
- h) assigning those pixels in the cluster characterized by low first stain intensity and low second stain intensity to background and removing such pixels from further analysis;
- i) assigning those pixels with first stain intensity and second stain intensity to either the first compartment or the second compartment based upon based on probability thereby defining a first marker defined sub-cellular compartment relative to a second marker defined sub-cellular compartment, wherein any of the assigning steps are performed using a k means clustering method to determine a cluster membership for each pixel, and wherein the method is automated.

14. A computer implemented method for defining a first marker defined sub-cellular compartment relative to a second marker defined sub-cellular compartment present in individual cells of interest contained in a tissue sample comprising:
- a) incubating the tissue sample with a first stain that specifically labels the first marker defined sub-cellular compartment, a second stain that specifically labels a second marker defined sub-cellular compartment,
- b) obtaining an image of each of the first and the second stain in the tissue sample using a microscope so as to obtain:
  - i) a first image of the first marker defined sub-cellular compartment;
  - ii) a second image of the second marker defined sub-cellular compartment; and
- c) determining the first and second stain intensity in each of the pixel locations in the first and the second image;
- d) plotting the pixels, where the axes of the plot comprise the intensity of the first stain and the intensity of the second stain;
- e) performing reiterative k-means clustering on the first and the second stain intensity in each of the pixel locations to calculate three clusters;
- f) assigning those pixels in the cluster characterized by high first stain intensity and low second stain intensity to the first compartment;
- g) assigning those pixels in the cluster characterized by high second stain intensity and low first stain intensity to the second compartment;
- h) assigning those pixels in the cluster characterized by low first stain intensity and low second stain intensity to background and removing such pixels from further analysis;
- i) assigning those pixels with first stain intensity and second stain intensity to neither the first compartment or the second compartment;

thereby defining a first marker defined sub-cellular compartment relative to a second marker defined sub-cellular compartment, wherein any of the assigning steps are performed using a k means clustering method to determine a cluster membership for each pixel, and wherein the method is automated.

* * * * *